United States Patent
Fenton

(10) Patent No.: US 10,613,066 B2
(45) Date of Patent: Apr. 7, 2020

(54) MONITORING POWER DEVICES

(71) Applicant: Roger Alan Fenton, Upland, CA (US)

(72) Inventor: Roger Alan Fenton, Upland, CA (US)

( * ) Notice: Subject to any disclaimer, the term of this patent is extended or adjusted under 35 U.S.C. 154(b) by 0 days.

(21) Appl. No.: 16/171,110

(22) Filed: Oct. 25, 2018

(65) Prior Publication Data
US 2019/0178863 A1 Jun. 13, 2019

Related U.S. Application Data

(62) Division of application No. 15/371,085, filed on Dec. 6, 2016, now Pat. No. 10,145,830.

(60) Provisional application No. 62/393,623, filed on Sep. 12, 2016, provisional application No. 62/393,630, filed on Sep. 12, 2016, provisional application No. 62/265,618, filed on Dec. 10, 2015.

(51) Int. Cl.
| | |
|---|---|
| *G01N 33/00* | (2006.01) |
| *G01K 13/00* | (2006.01) |
| *G01K 13/02* | (2006.01) |
| *G01L 7/00* | (2006.01) |
| *G01N 33/26* | (2006.01) |
| *G01R 31/44* | (2020.01) |
| *G01R 31/02* | (2006.01) |

(52) U.S. Cl.
CPC ......... *G01N 33/0036* (2013.01); *G01K 13/00* (2013.01); *G01K 13/02* (2013.01); *G01L 7/00* (2013.01); *G01N 33/26* (2013.01); *G01R 31/44* (2013.01); *G01R 31/027* (2013.01)

(58) Field of Classification Search
None
See application file for complete search history.

(56) References Cited

U.S. PATENT DOCUMENTS

| | | | | |
|---|---|---|---|---|
| 4,096,754 A | * | 6/1978 | Beveridge, Jr. | ..... G01L 19/0007 137/317 |
| 4,456,899 A | * | 6/1984 | Matthes | .................. H01F 27/12 336/55 |
| 5,279,795 A | | 1/1994 | Hughes et al. | |

(Continued)

FOREIGN PATENT DOCUMENTS

| | | | | |
|---|---|---|---|---|
| CN | 203596242 | * | 5/2014 | ............. H01F 27/08 |
| GB | 289091 A | | 8/1928 | |

(Continued)

OTHER PUBLICATIONS

Non-Final Office Action for U.S. Appl. No. 16/171,220, filed Oct. 25, 2018 on behalf of Roger Fenton, dated Sep. 17, 2019. 15 pages.

*Primary Examiner* — Daniel S Larkin
(74) *Attorney, Agent, or Firm* — Steinfl + Bruno LLP

(57) ABSTRACT

An apparatus senses properties of a fluid. The apparatus has a pipe section, a valve, and an instrument. The pipe section has an envelope, through which a flow of the fluid is coupled between a tank of an electrical power device and a cooling device. The envelope is disposed about a longitudinal axis, and has a penetration disposed laterally, relative to the longitudinal axis. The valve is disposed within the one or more penetrations and has a closed position and an open position. The instrument is operable for the sensing of the fluid properties, and has a probe disposed in contact with the fluid through the valve in the open position.

9 Claims, 12 Drawing Sheets

(56) References Cited

U.S. PATENT DOCUMENTS

| | | | |
|---|---|---|---|
| 5,936,715 A * | 8/1999 | Shapanus | G01N 33/2841 |
| | | | 356/70 |
| 6,323,655 B1 * | 11/2001 | Fu | G01R 31/1281 |
| | | | 324/536 |
| 7,991,503 B2 | 8/2011 | Gass et al. | |
| 10,145,830 B2 | 12/2018 | Fenton et al. | |
| 2002/0083781 A1 * | 7/2002 | Golner | G01N 1/14 |
| | | | 73/863.83 |
| 2011/0291674 A1 * | 12/2011 | Hosokawa | H01F 27/402 |
| | | | 324/658 |
| 2014/0053626 A1 * | 2/2014 | Jeffrey | G01N 33/2841 |
| | | | 73/19.1 |
| 2015/0090054 A1 * | 4/2015 | Leidner | G01N 33/1886 |
| | | | 73/866.5 |
| 2017/0168034 A1 | 6/2017 | Fenton et al. | |
| 2019/0064133 A1 | 2/2019 | Fenton et al. | |

FOREIGN PATENT DOCUMENTS

| | | | | |
|---|---|---|---|---|
| KR | 10-2008-0003273 | * | 1/2008 | H01F 27/12 |
| WO | WO 2015/0678444 | * | 5/2015 | G01N 33/28 |

* cited by examiner

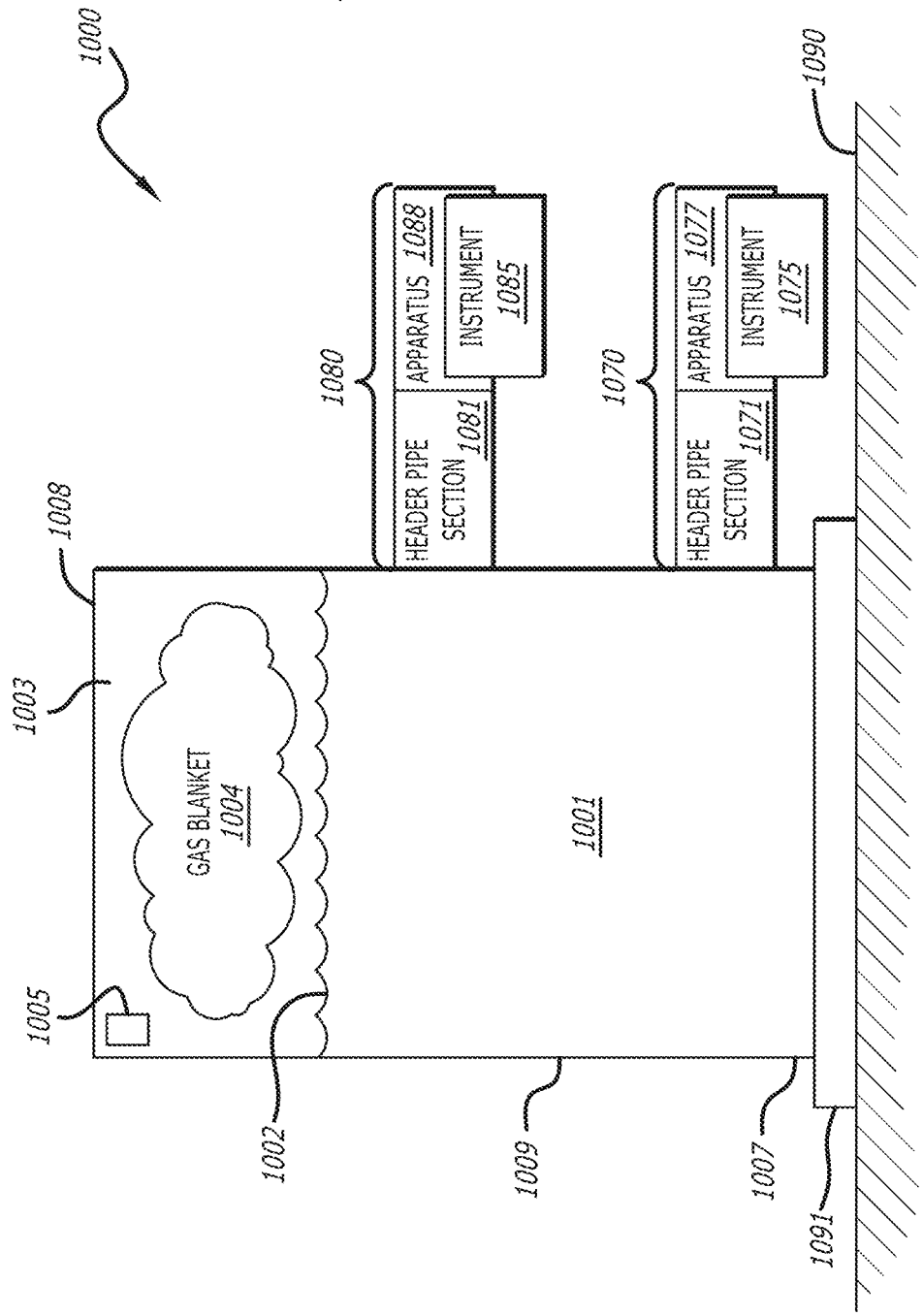

MONITORING POWER DEVICES

CROSS REFERENCE TO RELATED APPLICATIONS

The present application is a divisional of and claims priority to U.S. Non-Provisional Application No. 15/371,085 filed on Dec. 6, 2016, now U.S. Pat. No. 10,145,830, which, in turn, claims priority to U.S. Provisional Application No. 62/393,623 filed on Sep. 12, 2016, U.S. Provisional Application No. 62/393,630 filed on Sep. 12, 2016, and U.S. Provisional Application No. 62/265,618 filed on Dec. 10, 2015, the disclosures of all of which are incorporated herein by referenced in their entirety.

TECHNOLOGY

Embodiments of the present invention relate, generally, to power equipment. More particularly, example embodiments of the present invention relate to monitoring electrical devices.

BACKGROUND

In general, electrical power systems perform operations related to producing and delivering electricity used in industry, commerce, households, and other activities. The operations relate to generation, transmission, distribution, and control of electrical power, and comprise functions of various components of the systems, such as transformer and reactor devices.

Transformer devices are operable for inducing a flow of electrical power from a first circuit, having a first voltage level, in at least a second circuit, having a second voltage level, which may differ from the first voltage level. With "step-up" power transformers, for example, the second voltage level is greater than the first voltage level.

With "step-down" transformers, the second voltage level is less than the first voltage level. The first and second voltage levels may sometimes be equal, and the transformer operable for driving power flow in a "load side" one of the circuits, inductively, from the other "source side" circuit, while isolating direct conduction between the first and the second circuits.

Power transformers may comprise at least a pair of conductive coils per phase. One coil of the pair corresponds to the first voltage level, and the other to the at least second voltage level. The first voltage level and the second voltage level are related according to a ratio of a number of turns of the conductors in each of the respective coils of the pair.

The power transformers may operate at or near a frequency of 60 Hertz (Hz) in some terrestrial U.S. power generation, transmission, and distribution applications (50 Hz in some other places). Some power transformers may operate over a range near 400 Hz, which comprises a useful frequency in some power applications. Over the operating frequency ranges of the transformer, inductive coupling between each coil of the phase may be promoted with use of a high inductance core.

High inductance cores may comprise materials of low magnetic reluctance, such as iron, some alloys, and some other metals. The cores may be configured, e.g., as assemblies of independent laminated sheets, insulated from each other electrically to minimize inefficiencies related to hysteresis, eddy currents, and other losses.

Power devices also comprise one or more materials of high dielectric strength, configured to electrically insulate the coils from each other and from the core, and the windings of each coil from the other windings. The dielectric properties, and the durability of the insulating materials, are significant to the operation of the transformers, especially at high voltage levels.

The insulating materials may comprise fluids, such as oil, silicone related materials, organic liquids, mineral oils, and/or other nonconductive liquids. Paper, fiber, fiberglass, fabric, plastic and/or other solid materials may also be used to electrically insulate portions of the coils. The core and the coils may be supported mechanically with components of a structural framework of the transformer, and immersed in the liquid insulation material within a tank. The tank comprises a structural body of the transformer.

During operation, power devices may generate heat. The heat generated during operation of the power devices may be transferred, via a thermal working fluid, to a heat sink such as the surrounding atmosphere. In addition to providing the electrical insulation function, the insulating fluids may function, further, as the thermal working fluid in relation to cooling the transformer. As such, the fluid may circulate between the tank, in which the heat is generated by components of the transformer, and an atmospheric radiator (or other) heat exchanger, with which the heat is transferred to the heat sink.

It could be useful in general, therefore, to promote reliability in the operation of electrical power devices such as transformers and reactors. In furtherance of the promotion of reliable electrical power device operations, it could also be useful to sample the insulating fluids and to test properties of the sampled fluids characteristic of ongoing effectiveness. It could be useful, further, to provide for monitoring the properties of the power device insulating fluids over time, with continuous or on-demand availability of the sampling and testing, without interrupting the operations of the power device, and/or without disrupting the supply, flow, or utility of the fluids, in real time, during the operations of the power device.

SUMMARY

Accordingly, example embodiments of the present invention relate to the promotion of reliable electrical power device operations. Example embodiments of the present invention also relate to monitoring the power device, including monitoring of insulating fluids of the power device, such as sampling and testing properties of the fluids that may characterize ongoing usefulness, and thus promoting associated reliability of operations of the power device. An example embodiment of the present invention relates, further, to monitoring the properties of the power device insulating fluids over time, with continuous and/or on-demand availability, and without interrupting the operations of the power device, or disrupting the real time supply, flow, or utility of the fluids during the power device operations.

An example embodiment of the present invention relates to an apparatus for monitoring, sampling, detecting and/or sensing (hereinafter "sensing") one or more properties of a fluid. The fluid may comprise an electrical insulating medium, a thermal working fluid, and a coolant of the power device.

The fluid testing apparatus comprises a pipe section, a valve, and at least one instrument. The pipe section comprises an envelope, such as a pipe wall. The pipe section couples the fluid, through the envelope, between a tank of an electrical power device and a cooling device. The envelope is disposed about a longitudinal axis, and comprises one or more penetrations. The penetrations are disposed laterally in relation to the longitudinal axis of the envelope.

The valve comprises a closed position and an open position. The valve is disposed within the one or more penetrations, and thus penetrate the envelope of the pipe section. An example embodiment may be implemented in which the valve comprises a ball valve.

The at least one instrument is operable for the sensing of the one or more fluid properties, and comprises a probe. The instrument probe is disposed, e.g., removably, in contact with the fluid through the valve in the open position. An example embodiment may be implemented in which the instrument probe is interchangeable, through the valve, with a probe of at least a second instrument.

The fluid flow is coupled through the header between the power device tank and the cooling device. The cooling device may comprise a heat exchanger, such as a radiator. The heat exchanger transfers the heat removed from the power device by the fluid is transferred to a heat sink.

The one or more fluid properties comprise one or more physical and/or chemical characteristic of the fluid. The instrument probe may operable for detecting two or more of the physical and/or chemical characteristics of the fluid. An example embodiment may be implemented in which the instrument probe is operable for detecting each of a plurality of the fluid characteristics. The instrument generates a signal based on the detected fluid characteristics.

An example embodiment relates to a system for monitoring an electrical power device, such as a transformer, reactor, etc. The instruments exchange data related to the signal generated based on the fluid characteristics with a network. The network may relate to a Supervisory Control and Data Acquisition (SCADA) system and/or telephone, communication, data networks. An example embodiment relates to a method for monitoring an electrical power device.

An example embodiment relates to an instrument for monitoring an electrical power device. The instrument is operable for detecting physical and/or chemical characteristics of the fluid of the power device. The instrument may be operable for detecting two of more of the fluid characteristics. The instrument is interchangeable with at least a second instrument. An example embodiment relates to a method for monitoring an electrical power device.

The foregoing summary is presented by way of example and illustration, and is not to be construed as limiting or restrictive in any sense. The foregoing summary presents a conceptual prelude in relation to some example features, functions, aspects and/or elements of embodiments of the present invention, and the manner in which the same may be implemented or accomplished, which are further explained within the following more detailed description of example embodiments and each figure ("FIG.") of the accompanying drawings referred to therein. The following figures are not drawn to any particular scale (unless a specific scale is expressly nominated in relation to a particular drawing of the figures, or a portion of the particular drawing).

BRIEF DESCRIPTION OF THE DRAWINGS

FIG. 10A depicts the example power device, according to an embodiment of the present invention;

DESCRIPTION OF EXAMPLE EMBODIMENTS

Figure 1:
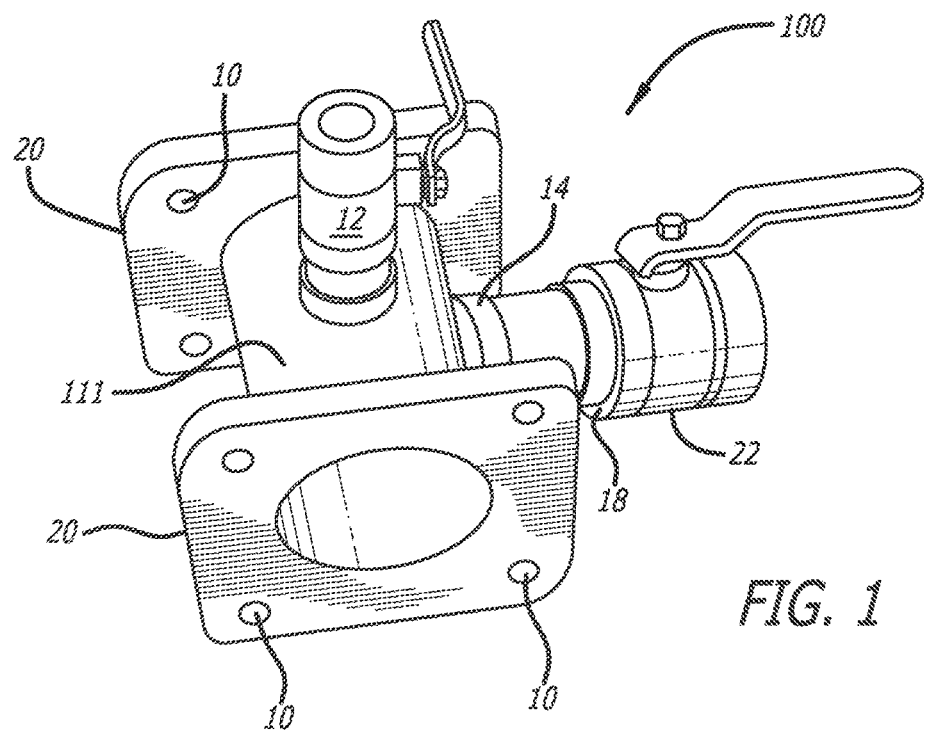
FIG. 1 depicts an example tubular assembly from a first view, according to an embodiment of the present invention.

Example embodiments of the present invention are described in relation to an apparatus for sensing properties of a fluid. The fluid may comprise an insulating fluid and coolant for an electrical power device, such as a transformer or reactor. The apparatus comprises a pipe section, a valve such as a ball valve, and at least one instrument.

The pipe section comprises an envelope, through which a flow of the fluid is coupled between a tank of the electrical power device and a cooling device, such as a radiator or other heat exchanger. The envelope is disposed about a longitudinal axis, and comprises one or more penetrations disposed laterally in relation to the longitudinal axis.

The valve is disposed within the one or more penetrations and has a closed position and an open position. The instrument is operable for the sensing of the fluid properties, and has a probe disposed in contact with the fluid through the valve in the open position. The fluid properties relate to one or more physical and/or chemical characteristics of the fluid. The instrument may be operable for detecting two or more of the physical/chemical fluid characteristics.

The instrument probe may be disposed removably through the valve. The instrument may be disposed, interchangeably, with the probe of at least a second instrument. Example embodiments relate to a system, an instrument, and a method for sensing the fluid properties.

The apparatus is operable for monitoring, sampling, detecting and/or sensing ("sensing") one or more properties of a fluid. The fluid may comprise an electrical insulating medium, a thermal working fluid, and a coolant of the power device. Example embodiments are described in relation to systems, instruments, methods, and networks for monitoring power devices such as transformers and reactors.

Example embodiments are described with reference to an example transformer device. A property of a fluid is sensed. The fluid is in a convective (and/or pump driven) flow, which circulates between a power device (such as a transformer or reactor) and an associated cooling device such as a radiator or other heat exchanger, is sensed. An assembly, which has a tubular section is installed, and couples the flow of the fluid, longitudinally between a tank of the power device and the cooling device. The tubular section is penetrated laterally, relative to the fluid flow. A valve located within one of the penetrations has a closed position, and an open position. A probe of an instrument, operable for sensing the property of the fluid, is placed in a contact with the flow of the fluid through the valve.

Overview.

A fluid may be used for electrically insulating and thermally cooling energized components and heat generated within electrical power devices, such as power transformers and reactors. The fluid may flow between a tank of an electrical power device and a cooling device associated therewith. Heat removed from the heat producing components of the electrical power device during operation is transferred by the flowing fluid to the cooling device, from which it may then be transferred to a heat sink. The cooling device may comprise a radiator. The radiator transfers the heat generated in the power device to an atmospheric heat sink. The cooling device may comprise a tube and shell heat exchanger, which transfers the heat generated in the power device to a secondary thermal working fluid, such as water circulating from a natural or artificial reservoir, cooling tower, etc.

An example embodiment of the present invention relates to an apparatus for monitoring a power device. The apparatus is operable for sampling, detecting and/or sensing ("sensing") one or more properties of a fluid of an electrical power device, such as a transformer, reactor, etc. The fluid testing apparatus comprises a pipe section, a valve, and at least one instrument.

Figure 9B:
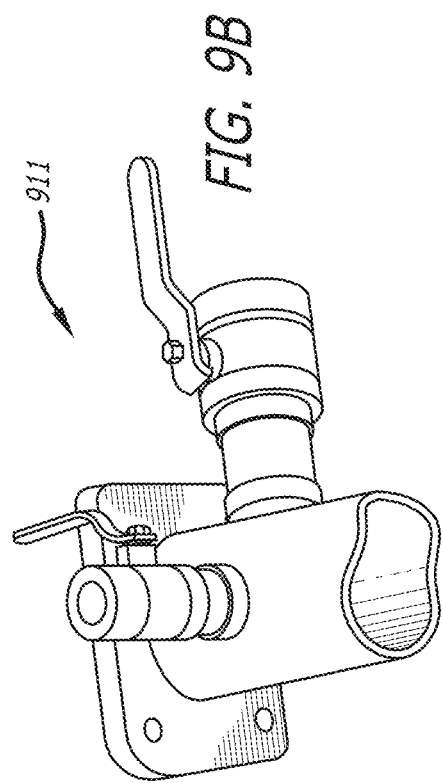
FIG. 9B depicts the example apparatus configured as a component of a header of the cooling device, according to an embodiment of the present invention.
Figure 9C:
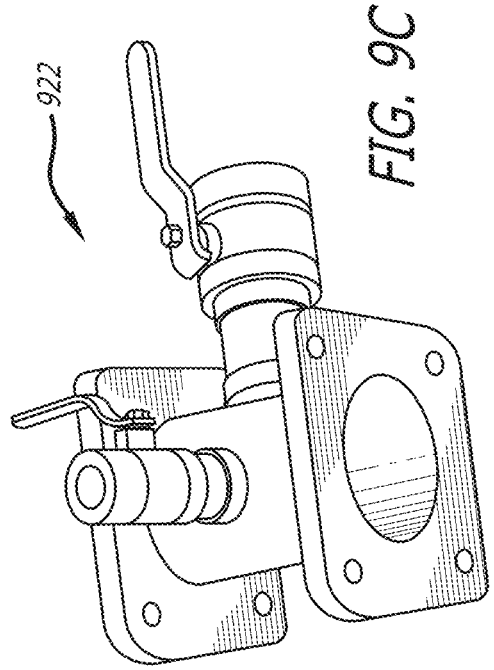
FIG. 9C depicts the example apparatus configured as a component of a header coupling fluid between the power device and the cooling device, according to an embodiment of the present invention.
Figure 9A:
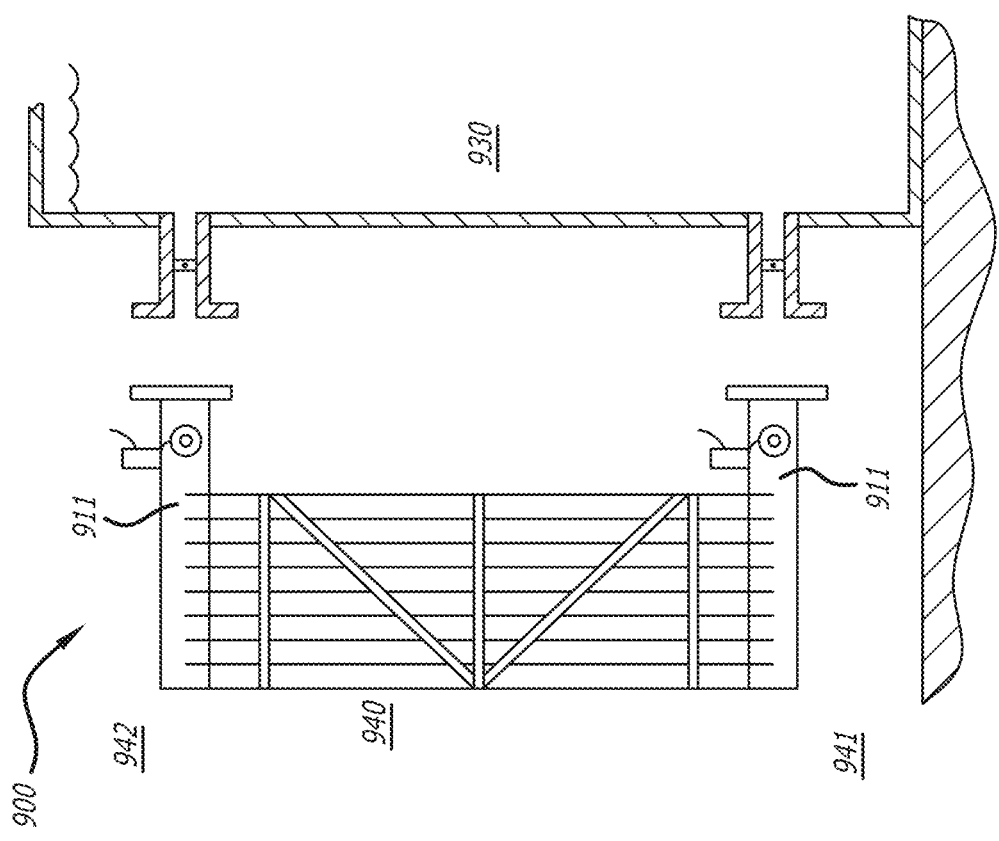
FIG. 9A depicts an example apparatus installed with a cooling device and a power device, according to an embodiment of the present invention.

FIG. 9A depicts an example installation 900, according to an embodiment of the present invention. An apparatus 911 is installed with a cooling device 940 and a power device 930. The cooling device 940 depicted in FIG. 9A comprises a radiator.

The apparatus 911 may be installed in the lower header 941 and/or in the upper header 942 of the cooling device. FIG. 9B depicts the example apparatus 911 configured as a component of the header 941 and the header 942 of the cooling device 940, according to an embodiment of the present invention.

The apparatus 911 may be installed between the power device 930 and the cooling device 940. FIG. 9C depicts the example apparatus 922 configured as a component into a header for coupling fluid between the power device and the cooling device, according to an embodiment of the present invention.

FIG. 10A depicts an example power device 1000, according to an embodiment of the present invention. The power device 1000 is described with reference to a transformer and comprises a tank 1009. The tank 1009 comprises a structural body of the transformer 1000 and a container of a fluid 1001. Electrically active components of the transformer 1000 such as conductive coils, sometimes referred to as "windings," and a magnetically permeable core are immersed in the fluid 1001. The fluid 1001 comprises a dielectric strength sufficient to provide electrical insulation to the electrically active components. The fluid 1001 comprises heat capacity and fluidity sufficient to remove heat generated by the electrically active components of the transformer 1000 during operation.

The tank 1000, and components of the transformer 1000, including the core and structural framework upon which the core and coils are supported, may be grounded electrically, relative to potentials associated with the electrically active coils of the transformer. An electrically neutral node within the windings may also be grounded. In some transformers and electrical systems, the node may be grounded directly, with effectively zero resistance (or other impedance) between the electrical node and the ground potential. In some other transformers and electrical systems, the node may be grounded with some resistance (and/or other impedance) added between the electrical node and the ground potential. Based on the characteristics of a particular electrical system, the grounding resistance (and/or other impedance) may comprise a high resistance (and/or other impedance) value, relative to a direct grounding connection. In another electrical system, the grounding resistance (and/or other impedance) may comprise a lower resistance (and/or other impedance) value, relative to the "high" values. A bottom 1007 of the tank 1009 may be disposed on a ground based pad 1091, which may be disposed set in earth, a foundation, on a pad, a platform and/or on a structure (1090). The tank 1009 comprises a top 1008 disposed vertically above the bottom 1007. The tank may be grounded directly.

A gas blanket 1004 may be disposed within a headspace 1003 of the tank 1009 above a surface 1002 of the fluid 1001. An instrument 1005 may be disposed within the headspace 1003 and operable for detecting ("sensing") one or more physical and/or chemical properties of the gas within the blanket 1004.

The fluid 1001 may be isolated and sealed within the tank 1009 from exposure to the external environment in which the transformer 1000 is disposed. A gas may be added within the tank 1009. The gas may comprise a relatively inert gas such as nitrogen ($N_2$, "N2"), a noble gas, or a mixture of gases. The gas 1004 is disposed over a surface 1002 of the fluid 1001 within the tank 1009. The fluid surface 1002 is thus covered with the gaseous blanket 1004. The gas blanket 1004 may be kept at a positive pressure, relative to the external atmosphere in which the transformer tank 1009 is enveloped. The positive gas blanket pressure may be maintained to deter or inhibit an inflow from the environment to the tank 1009, which could introduce a contaminant to the fluid 1001.

A lower header 1070 is coupled to a lower opening in the tank 1009 proximate to the bottom 1007 thereof. The lower header 1070 comprises a header pipe section 1071 and an apparatus 1077. The apparatus 1077 comprises an instrument 1075. The apparatus 1077 and the instrument 1075 comprise an apparatus and an instrument described herein with reference to an example embodiment of the present invention.

An upper header 1080 is coupled to an opening in the tank 1009 disposed vertically above the lower opening. Relative to the lower opening, the upper opening is disposed more proximate to the top 1008 of the tank 1009 and more distant from the tank bottom 1007. A volume of the fluid 1001 may be maintained in which a vertical level of the surface 1002 thereof covers the upper opening. The upper header 1080 comprises a header pipe section 1081 and an apparatus 1088. The apparatus 1088 comprises an instrument 1085. The apparatus 1088 and the instrument 1085 comprise an apparatus and an instrument described herein with reference to an example embodiment of the present invention.

Figure 10B:
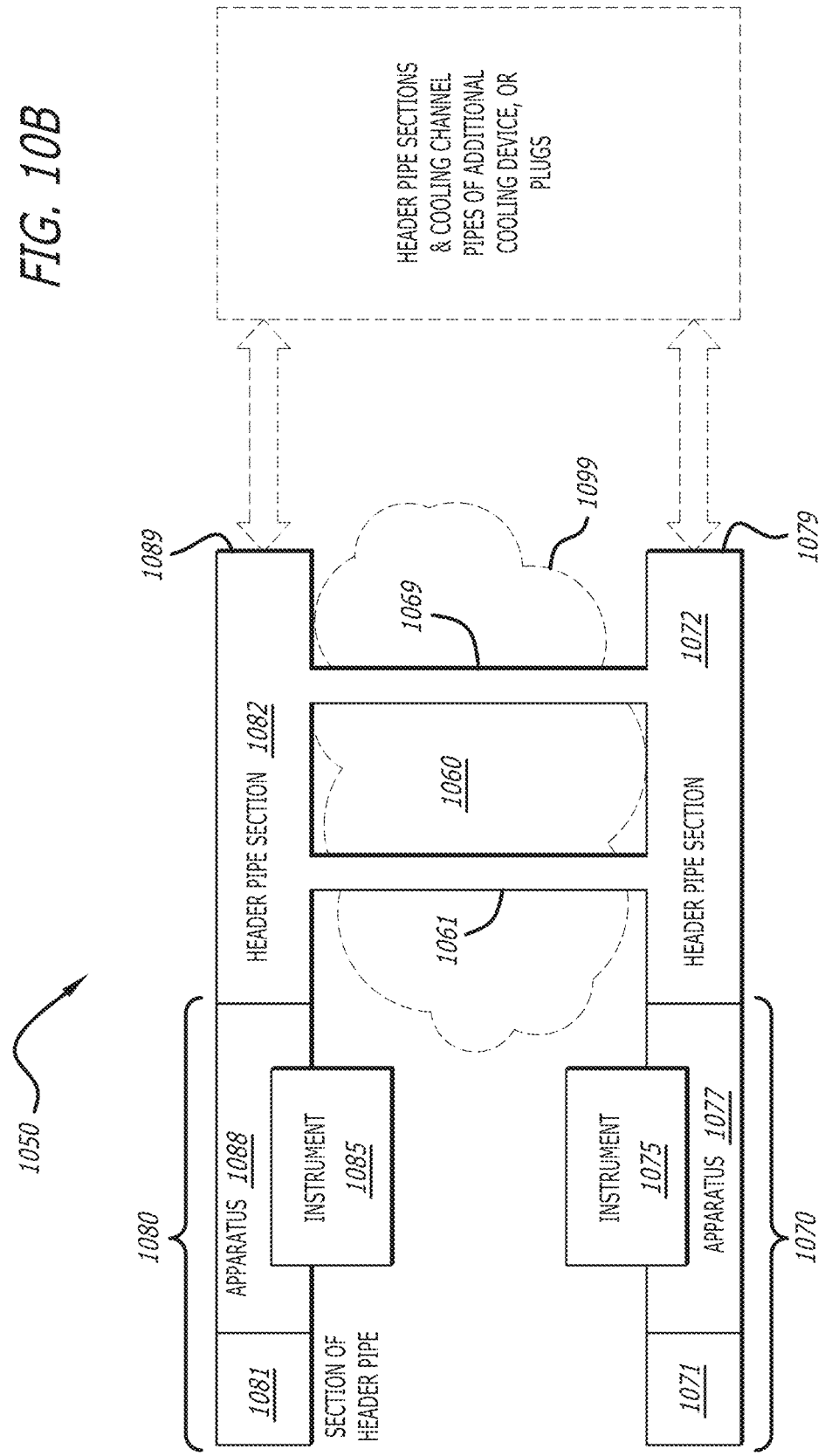
FIG. 10B depicts the example cooling device, according to an embodiment of the present invention.

During operation, the power device 1000 generates heat. The heat generated during operation of the power device 1000 may be transferred, via the thermodynamic working fluid 1001 and a cooling device, to a heat sink. The cooling device comprises a radiator or other heat exchanger. FIG. 10B depicts an example cooling device 1050, according to an embodiment of the present invention.

The cooling device 1050 is described with reference to an example radiator, which comprises an upper manifold 1089 and a lower manifold 1079. The upper manifold 1089 is coupled to the upper header 1080 (FIG. 10A), and the lower manifold 1079 is coupled to the lower header 1079 (FIG. 10A). The fluid 1001 absorbs heat produced during the operation of the transformer 1000. The heated fluid 1001 flows, e.g., convectively, to the radiator 1050 through the upper header 1080. The fluid 1001 flows through a cooling channel 1060 and into the lower header 1070, through which it returns, e.g., convectively, to the tank 1009 of the power device 1000. The convective flow of the fluid 1001 may be augmented by action of one or more pumps.

The cooling channel 1060 comprises an array of cooling pipes. The cooling channel 1060 pipe array comprises a cooling channel pipe 1061 and at least a second cooling channel pipe 1069. The heat absorbed from the power device 1000 by the fluid 1001 is transferred through the walls of the cooling channel 1060 pipes and radiated into the surrounding atmosphere 1099, which comprises the heat sink.

In addition to providing the electrical insulation function, the insulating fluid 1001 thus functions as the thermal working fluid to cool the power device 1000. The fluid 1001 comprises a coolant in relation to cooling the transformer. As such, the fluid circulates between the tank, in which the heat is generated by components of the transformer, and an atmospheric radiator (or other) heat exchanger, with which the heat is transferred to the heat sink.

The cooling device 1050 comprises a lower header pipe section 1072, which is operable as the lower manifold 1079, and an upper header pipe section 1082, which is operable as the upper manifold 1089. The cooling channel pipes 1060 are disposed between the lower header pipe section 1072 and an upper header pipe section 1082. The lower header pipe section 1072 is coupled to the lower header 1070. The upper header pipe section 1082 is coupled to the upper header 1080. The lower header 1070 comprises a header pipe section 1071. The upper header 1080 comprises a header pipe section 1081.

The apparatus 1077 comprises a portion of the lower header 1070, which is disposed between the header pipe section 1071 and the lower header pipe section 1072 of the cooling device 1050. The lower header pipe section 1072 of the cooling device 1050 may comprise the apparatus 1077. An example embodiment may thus be implemented in which the apparatus 1077 comprises a component of the cooling device 1050.

The apparatus 1088 comprises a portion of the lower header 1080, which is disposed between the header pipe section 1081 and the upper header pipe section 1082 of the cooling device 1050. The upper header pipe section 1082 of the cooling device 1050 may comprise the apparatus 1088.

An example embodiment may thus be implemented in which the apparatus 1088 comprises a component of the cooling device 1050.

An example embodiment of the present invention relates to an apparatus for monitoring the power device 1000. One or more of the apparatus 1077 or the apparatus 1088 are operable for sampling, detecting and/or sensing ("sensing") the one or more physical and/or chemical properties of a fluid of the electrical power device, transformer 1000. The fluid testing apparatus 1077 and 1088 each comprise a pipe section, a valve, and at least one instrument.

Figure 11A:
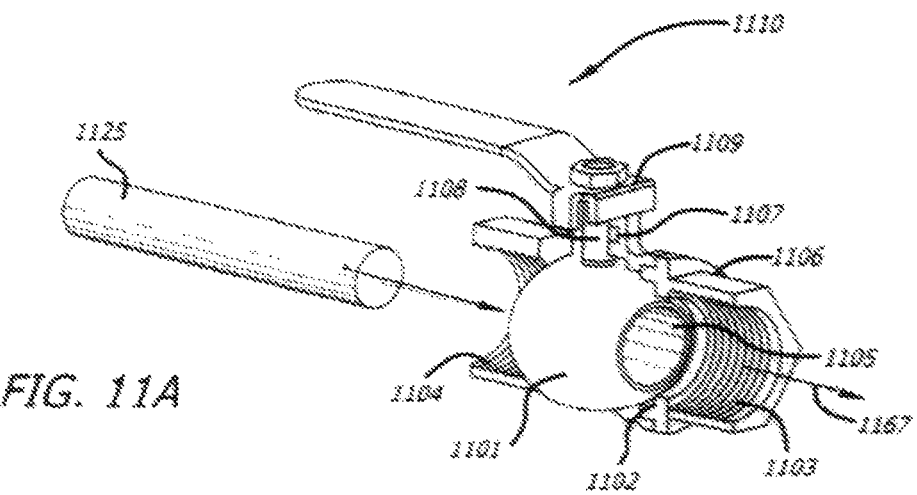
FIG. 11A depicts an example valve, according to an embodiment of the present invention.
Figure 11B:
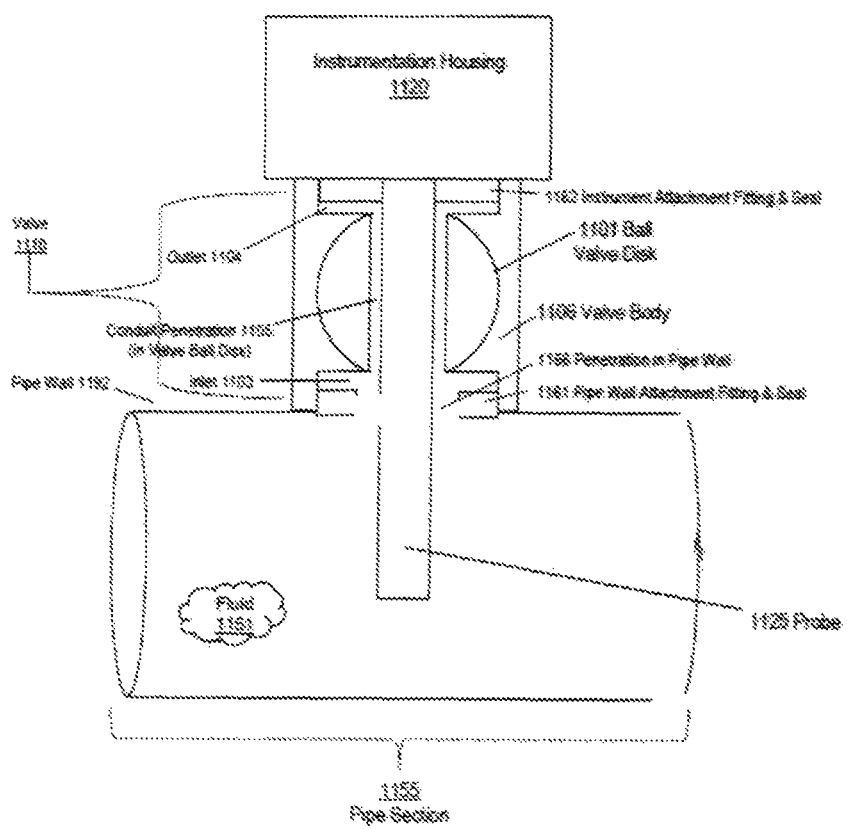
FIG. 11B depicts an example apparatus, according to an embodiment of the present invention.

FIG. 11B depicts an example apparatus 1100, according to an embodiment of the present invention. The apparatus 1100 comprises a pipe section 1155, a valve 1110, and at least one instrument 1120. The pipe section 1155 comprises an envelope 1192, such as a pipe wall. The pipe section 1155 couples the fluid 1151, through the envelope 1192, between a tank of an electrical power device and a cooling device. The envelope 1192 is disposed about a longitudinal axis thereof, and comprises one or more penetrations 1166. The penetrations 1166 are disposed laterally in relation to the longitudinal axis of the envelope 1192.

FIG. 11A depicts an example valve 1110, according to an embodiment of the present invention. The valve 1110 comprises a closed position and an open position. In FIG. 11A, the valve 1110 is depicted in the open position. The valve 1110 is disposed within the one or more penetrations 1166, and thus penetrate the envelope 1192 of the pipe section 1155. An example embodiment may be implemented in which the valve 1110 comprises a ball valve.

The at least one instrument 1120 is operable for the sensing of the one or more fluid properties, and comprises a probe 1125. The instrument probe 1125 is disposed, e.g., removably, in contact with the fluid 1151 through the valve 1110 in the open position. An example embodiment may be implemented in which the instrument probe 1125 is interchangeable, through the valve 1110, with a probe of at least a second instrument.

The pipe section 1155 of the fluid testing apparatus 1100 may be disposed between opposing sections of a header. The opposing sections of the header may comprise a first section and an opposite second section. The first section comprises an end of the header disposed towards the tank of the power device. The second section comprises an end of the header disposed in a direction opposite from the direction of the power device tank. The pipe section 1155 may comprise a portion of an integral header.

The pipe section 1155 may be fastened between the opposing sections of the header. For example, the pipe section 1155 may comprise a pipe section that is independent, relative to the first and second header sections. The pipe section 1155 of the apparatus 1100 may comprise an independent pipe section, disposed between a pair of flanges. The flanges of the pipe section 1155 may be fastened (e.g., bolted) and sealed (e.g., with a gasket) between the first and the second sections of the header.

The fluid flow is coupled through the header between the power device tank and the cooling device. The cooling device may comprise a heat exchanger, in which the heat removed from the power device by the fluid is transferred to a heat sink.

For example, the heat exchanger may comprise a radiator or a tube and shell type heat exchanger. Tube and shell heat exchangers transfer heat from the fluid to a liquid coolant heat sink. A radiator transfers the heat to an atmospheric heat sink. The cooling device may comprise one or more headers, through which the fluid flows. For example, a radiator may comprise a pair of header components.

As described with reference to FIG. 10B, the pair of header components of the radiator may comprise a first header component, and a second header component. The first header component may comprise a lower header of the radiator, and the second header component may comprise an upper header of the radiator (or vice versa). As described with reference to FIG. 10A, the lower header is attached to the transformer tank in a position disposed vertically below a position on the tank at which the upper header is attached. The radiator may also comprise a plurality of cooling channels with which the first header component and the second header component are coupled.

As described with reference to FIG. 10B, each of the cooling channels may comprise a channel pipe, coupled at opposite ends to each of a pair of corresponding penetrations on each of the headers of the radiator. The first header and the second header support the channel pipes between them, and distribute the flow of the fluid through them as a manifold. The fluid flows from a first of the header components, through the penetration in the first header to which a cooling channel is coupled, and through the cooling channel.

The heat is transferred from the fluid to an inner surface of a wall of the cooling channels, conducted through the wall, and radiated, ultimately, from an outer surface of the cooling channel wall to the atmosphere. The fluid then flows from the cooling channel, through the penetration to which the channel is coupled at its opposite end, and into the second header component, from which it may flow, convectively (and optionally, with an action of a pump) back to the tank of the electrical device.

An example embodiment may be implemented in which the pipe section 1155 of the fluid testing apparatus 1100 comprises a section of the first header component, and/or the second header component of the cooling device. For example, each of the first and the second cooling device header components comprises a pipe. The header component pipes each comprise a tank-side end oriented towards the power device tank, and a far-side end opposite from the tank side end and oriented in a direction opposite therefrom.

The tank side end of the header component pipe may be attached to the power device tank, as described with reference to FIG. 10A. An opening in the tank side end of the pipe admits the fluid to flow between the power device tank and the header component. The channel pipes may be disposed in a manifold array between the tank-side end of the header pipe, and the header pipe end opposite from the tank side end. Each of the header pipes may comprise a tank-side pipe segment disposed between the tank end and the array of channel pipes, and/or a far-side pipe segment disposed between the array of channel pipes and the far-side end.

An example embodiment may be implemented in which the pipe section of a fluid testing apparatus comprises a section of the tank-side pipe segment of one or more of the header components. An example embodiment may also (or alternatively) be implemented in which the pipe section of a fluid testing apparatus comprises a section of the far-side pipe segment of one or more of the header components.

The end of the header pipe opposite from the tank end may be sealed with a plug, e.g., to prevent leakage of the fluid therefrom. The end of the header pipe opposite from the tank end may be, alternatively, open to the flow of the fluid. For example, the cooling device may comprise a tank-side stage in an array of multiple cooling device stages, which may be assembled into a unitary multi-stage cooling device. The end of the header pipe opposite from the tank end may allow the flow of the fluid to continue to or from the tank-side openings of the header pipes of a subsequent stage.

The one or more fluid properties comprise one or more physical and/or chemical characteristics of the fluid. The instrument probe may operable for detecting two or more of the physical and/or chemical characteristics of the fluid. An example embodiment may be implemented in which the instrument probe 1125 is operable for detecting ("sensing") each of a plurality of the fluid characteristics.

An example embodiment of the present invention relates to a system for monitoring an electrical power device. The power device monitoring system comprises one or more instruments operable for sensing one or more properties of a fluid of the power device, and for generating a signal corresponding to each of the one or more sensed properties. The one or more instruments each comprise a probe disposed in contact with the fluid through a valve. The valve is mounted within a lateral envelope of a pipe, through which a flow of the fluid is coupled longitudinally between a tank of the power device and a cooling device, such as a heat exchanger. The instrument probe is disposed, removably, into the contact with the fluid through the valve, with the valve disposed in the open position.

For example, the valve 1110 may comprise a ball valve, as depicted in FIG. 11A. The ball valve 1110 comprises a solid spherical or spheroidal disk 1101. The disk 1101 is penetrated with a tubular conduit 1105, which may be disposed in an alignment along the diameter of the disk (or parallel thereto). In the closed-valve position, the disk 1101 may seat against a conforming inner surface of a body 1106 of the valve 1110 to block a flow of the fluid 1151 through the valve. The disk 1101 may be rotated into the open-valve position by an actuator mechanism 1109, which applies torque via a shaft 1108 coupled to the disk 1101. With the valve 1110 in the open position, the conduit 1105 aligns with an opening 1102 in an inlet 1103 on one end of the valve body 1106 and an outlet 1104 on a second end of the valve body 1106, opposite from the inlet end 1103, and allows the fluid 1151 to enter therein. A gland 1107 may inhibit weeping or leakage of the fluid 1151 along a shaft or other component of the actuator 1109.

Moreover, an inside diameter of the conduit 1105 exceeds a maximum dimension of a contour of an outer surface of the instrument probe 1125. The diameter of the conduit 1105 thus suffices to accommodate an insertion of the instrument probe 1125 through the conduit 1105 into and/or through the valve 1110, through the penetration 1166 within the pipe wall 1192 of the pipe section 1155, and into contact with the fluid 1151 therein. The instrument probe 1125 comprises one or more sensors disposed on, or accessible through the surface of the probe.

Exposed to contact with the fluid 1151 in the valve 1110 and/or within the pipe envelope 1192, the sensors of the probe 1125 are operable in relation to the detection of the one or more physical and/or chemical characteristics of the fluid. The probe may comprise an array of sensors, each operable in relation to detecting at least one of the chemical and/or physical properties of the fluid. In an example embodiment, the probe sensors are operable for detecting at least two of the physical and/or chemical characteristics of the fluid 1151. Upon exposure to the fluid for example, the probe sensors may generate or develop a signal.

The instrument 1120 may be attached, or disposed proximate to the outside of the valve body 1106. For example, a component of the instrument 1120 from which the probe 1125 protrudes may be attached to the outlet 1104 of the valve 1110. The valve 1110 may compatibly attach to the instrument 1120 with an attachment fitting and seal assembly 1162. The instrument attachment and seal assembly 1162 may comprise a threaded fitting compatible with complementary threading proximate to the outlet 1104 of the valve 1110, and a packing material, such as a tape, gasket, or washer.

The valve 1110 may attach to the pipe wall 1192 at the penetration 1166 therein, with an attachment fitting and seal assembly 1161. The pipe wall attachment and seal assembly 1161 may comprise a threaded fitting compatible with complementary threading proximate to the inlet 1104 of the valve 1110, and/or the penetration 1166 in the pipe wall 1192, and a packing material, such as a tape, gasket, or washer.

The signal generated/developed by the sensors of the probe 1125 may be processed (e.g., amplified, filtered, digitized, encoded, transcoded, packetized, multiplexed, etc.) electronically by the instrument 1120. The instrument component is also operable for exchanging data, related to the processed sensor signal with a network.

The power device monitoring system comprises a network operable for exchanging the data with the one or more instruments. The monitoring of the electrical power device comprises processing related to the exchanged data. The network may comprise a data, communication, and/or telephone network. The network may comprise a Supervisory Control and Data Acquisition (SCADA) system, associated with an electrical power grid or industrial process. The signal communicated over the network may be stored, signaled, and/or processed further by computers and other entities of the network.

The instrument probe 1125 may also be withdrawn from the valve 1110 through the tubular conduit 1105 therein. The probe 1125 may thus be placed into contact with the fluid 1151 through the open valve 1110, interchangeably, with a probe of at least a second instrument.

The fluid 1151 may also thus be sampled with the instrument 1120. For example, a portion of the fluid 1151 may be stored within an inner volume of the probe 1125 and/or a cavity of the instrument 1120 accessible therewith and withdrawn. The sampled fluid may be subject to analytic testing, diagnosis, chemical analysis, measurement of physical properties, etc.

In an example embodiment of the present invention, the system may relate to an apparatus for sensing the properties of the fluid, as described herein. The pipe of the system may be disposed in a header, which couples the tank of the power device and the cooling device. The header may comprise an upper header and/or a lower header, relative to each other, a corresponding lower vertical position on the power device tank and/or the cooling device, and/or a corresponding upper vertical position on the power device tank or the cooling device.

The one or more instruments of the system may comprise a first instrument and at least a second instrument. A probe of the first instrument is disposed in association with a first of the lower header or the upper header. A probe of the second instrument is disposed in association with a second of the lower header or the upper header. The second header is disposed in the vertical position opposite from that of the first header. The second instrument is also operable in relation to the sensing of the power device fluid property.

The fluid properties sensed by the instruments may relate to a temperature and a pressure of the fluid, and a moisture content thereof. Thus, the system may be operable for monitoring the power device in relation to a moisture hysteresis process occurring during operation, a differential pressure between different portions of the fluid, such as the upper header and the lower header, as the fluid flows in circulation between the power device and the cooling device, etc.

In addition to the temperature and/or the pressure, the physical and/or chemical characteristics of the fluid sensed by the instrument (and/or analyzed in relation to samples of the fluid withdrawn therewith) may relate to monitoring the power device in relation to one or more conditions related to its operation and/or maintenance. For example, the sensed the physical/chemical characteristics of the fluid may relate to monitoring the moisture hysteresis and/or the condition of internal components of the power device, such as the solid insulation, windings, and/or electromechanical components such as a load tap changer (LTC).

An example embodiment may be implemented in which the monitoring of the fluid characteristics relating to moisture content of the fluid, moisture hysteresis processes that may be occurring during operation of the power device, and/or characteristics of the fluid associated with the moisture content and/or moisture hysteresis is performed, at least in part, as described in the International Patent Application Publication No. WO 2015/067844 A1, which is incorporated by reference herein in its entirety. The Int'l Pat. Appl. No. WO 2015/067844 relates to Int'l Pat. Appl. No. PCT/FI2014/050359 filed 13 May 2014 by Applicant Vaisala Oyj of Finland for a "Method and Apparatus for Continuous Monitoring of Quality and Moisture Parameters of Liquids" by Inventor Oleg Roizman (hereinafter "Roizman").

The sensed the physical/chemical characteristics of the fluid may relate to detecting an indication of a condition or material related to electrical events occurring and/or developing therein, such as partial discharge and/or arcing. The sensed the physical/chemical characteristics of the fluid may relate to detecting a concentration level of an oxidant, oxidizer, or gas such as hydrogen or oxygen, which may be dissolved or suspended in the fluid.

The sensed physical/chemical characteristics of the fluid may relate to photometric, spectrometric, or chromatographic analysis. The sensed the physical/chemical characteristics of the fluid may relate to detecting a level of a moisture content, acidity, and/or alkalinity level of the fluid. The sensed physical/chemical characteristics of the fluid may relate to a measurement of viscosity, interfacial tension (IFT), conductivity, and/or dielectric strength. The sensed physical/chemical characteristics of the fluid may relate to a presence, identity, and/or level of concentration of a contaminant material suspended or dissolved within the fluid.

The probe disposed in the fluid may comprise a first probe. The tank of the power device may comprise a head space over an upper surface of the fluid. A gaseous atmosphere may be is disposed within the head space of the tank. The gas blanket may comprise a relatively inert gas such as dry nitrogen ($N_2$, 'N2'), or a dry noble gas, which blankets the upper surface of the fluid. For example, the head space may be pressurized with the gas. The gas blanket may be maintained at a positive pressure relative to the barometric pressure of the atmosphere, which may deter ingress of air and moisture. In an example embodiment, the system comprises at least one second probe.

The at least second probe is disposed in the head space, and is operable for sensing one or more physical or chemical characteristics of the gas blanket. The physical/chemical properties of the gaseous atmosphere may comprise a temperature and/or a pressure of the gas.

The physical/chemical properties of the gaseous atmosphere may relate to an indication of a condition or material related to an electrical event or condition, such as partial discharge and/or arcing event occurring within the electrical device. The physical/chemical properties of the gaseous atmosphere may relate to a concentration of an oxidant, oxidizer, or oxide within the gaseous atmosphere. The physical/chemical properties of the gaseous atmosphere may relate to a concentration of a gas component (e.g., hydrogen) of the gaseous atmosphere.

The physical/chemical properties of the gaseous atmosphere may relate to photometric, spectrographic, and/or chromatographic analysis. The physical/chemical properties of the gaseous atmosphere may relate to a detection of a presence of a contaminant material within the gaseous atmosphere, an identity of the contaminant material, and/or a concentration of the contaminant material. The physical/chemical properties of the gaseous atmosphere may relate to an indication of a condition of one or more components of the power device, which are disposed within the power device tank. The physical/chemical properties of the gaseous atmosphere may relate to a differential pressure between portions of the fluid disposed at different positions within the system, an indication of a level or volume of the fluid within the tank of the power device, and/or a differential pressure between the header space and a portion of the fluid in one or more of the lower header or the upper header.

In an example embodiment, the instrument 1120 is operable for monitoring properties of the fluid 1151 relating to temperature, and levels of hydrogen, moisture, oxidation, acidity, and contamination. The probe 1125 may comprise a matrix of beads, which are sensitive to detection of moisture, acidity, oxidation, contamination, and temperature of the fluid 1151.

A bead matrix sensor may be implemented in relation to the probe 1125 and the instrument 1120 as described in one or more of U.S. Pat. No. 5,435,170 to Voelker, et al., U.S. Pat. No. 5,777,210, to Voelker, et al., U.S. Pat. No. 5,789,665 to Voelker, et al., and/or U.S. Pat. No. 7,521,945 to Hedges, et al., which are each incorporated herein by reference. Hereinafter, these references are referred to collectively as the "Voelker and Hedges references."

The probe 1125 may comprise a sensor operable for monitoring pressure and hydrogen content in the fluid 1151 and/or the gas 1004. The pressure and hydrogen sensitive probe 1125 may be implemented as described in one or more of the Voelker and Hedges references.

Example Diagnosis of Power Device Operating Conditions.

The probe 1125 may be sensitive to detecting pressure, partial discharge indications, temperature, and combinations of properties of the fluid 1151. Two or more probes may be used to detect differential pressure and/or partial differential pressure between different portions of the fluid 1151. For example, two probes may be used to detect a differential pressure between a portion of the fluid 1151 in the upper header 1080, and a portion of the fluid 1151 in the lower header 1070.

A probe of the gas instrument 1005 may be sensitive to detecting a pressure of the gas blanket 1004. In combination with a pressure transducer associated with the probe 1125 of the instrument 1075, a differential pressure between the gas blanket 1004 and the portion of the fluid 1151 in the lower header 1070 may be used, along with a measurement of average temperature, to compute values relating to the volume of the fluid 1151, the level of the fluid 1001 within the 1009, and to detect various conditions, such as may relate to leakage of the fluid, rising (or falling) pressure within the tank 1009, abnormalities (e.g., overpressure, under-pressure, etc.) relating to gas pressure, flow restrictions in desiccant breather, changes in the pressure of winding clamping mechanisms, and/or impacts of ballistic projectiles upon the tank 1009 of the power device 1000, the cooling device 1050, the lower header 1070, the upper header 1080, and associated pipes, plumbing, seals, and equipment.

Static and dynamic measurements of the pressure of portions of the fluid 1151 can provide information on various operating conditions associated with monitoring transformer or reactor related power devices. The monitored operating conditions may relate to level and volume of the fluid 1151, pressure within the tank 1009 and/or other portions of the system, operational condition of a desiccant breather, integrity of clamping, which may provide structural support and mechanical strength to the coil windings of the electrically active portions of the power devices, and the impact of ballistic projectiles.

The probes 1125 and the instruments 1120 may be operable to detect acoustic, ultrasonic, vibrational, and/or mechanical oscillations within and/or throughout various portions of the fluid 1151, which may be used in relation to associated pressure detection and detection of an occurrence of partial discharge and/or arcing events, ballistic impacts, and vibration of mechanical and/or structural components within the power device 1000 and/or the cooling device 1050.

Pressure transducers associated with the probe 1125 and instrument 1120 may comprise various accuracy classes, and/or thermal compensation. High-accuracy models with thermal compensation may be used for monitoring power transformers. Pressure transducers with ranges of approximately 0-5 pounds per square inch (psi), e.g., gauge, may be used for monitoring relatively small transformers.

The fluid 1151 may comprise various types of insulating liquids with heat capacities and fluidity properties sufficient for cooling liquid-immersed transformers and reactors. Different fluids may vary in properties relating to their respective densities, rates of thermal expansion, viscosity, and IFT.

The temperature of the fluid 1151 may be measured with temperature sensors associated with the probes 1125 and instruments 1120 immersed in different portions of the fluid. For example, the temperature of the fluid 1151 may be detected with the instrument 1075 in the lower header 1070, and with the instrument 1085 in the upper header 1080.

The tank 1009 may comprise a shape that may be other than simple. The level and average temperature of the fluid 1001 within the tank 1009 may be determined with the pressure measurements and computations based on a geometry of the tank. The monitoring of the pressure of the fluid 1001 can be used to detect changes in the height of the surface 1002 of the fluid within the tank 1009 and compute associated changes in the volume of the fluid. Also, the impact of ballistic projectiles such as a bullet on the tank 1009, the radiator 1050 or cooler, or associated piping, plumbing, or equipment may be detected as a sudden impulse in the pressure of the fluid, and/or acoustic or ultrasonic vibrations or mechanical impulses or waves, which can be used to initiate monitoring for leakage, such as computation of a leak analysis algorithm.

Embodiments may relate to detecting abnormal rises (or falls) in the pressure of the fluid, a rate of change in the pressure, and computations related to an expected time remaining until pressure events associated with actuation of a pressure-relief device (PRD) set to trigger at a particular pressure set point rating. The time expectations, and/or the possibility of occurrence of a release of fluid from the system, blockage of a desiccant breather, and/or gagging, blocking, or other mechanical disability related to an operation of the PRD may also be predicted. Pressure and/or acoustic, sonic, ultrasonic, or vibration transducers with a response rate greater than or equal to two (2) Kilohertz (kHz) may be used to detect pressure vibrations that may be associated with loose core clamping. Such pressure vibrations may be measured accurately in multiples of 120 Hertz (Hz) over a range of 120 Hz to 960 Hz. Pressure detection may be performed according to U.S. patent application Ser. No. 13/861,689, filed 12 Apr. 2013 by Watson for "Electronic Liquid Level Sensing Device and Gauge for Liquid-immersed Power Transformers, Reactors and Similar Equipment," (hereinafter "Watson") which is incorporated herein by reference.

The instrument 1120 may be operable for detecting symptoms of partial discharge (PD) occurring in the power device 1000. The probe 1125 may be sensitive to detection of acoustic, sonic, and/or ultrasonic mechanical vibrations over an ultra-high frequency (UHF) range of 300 Megahertz (MHz) to 1.5 Gigahertz (GHz), inclusive; high frequency (HF) vibrations relative to ground over a range of 0.5 MHz to 50 MHz, inclusive; and/or over a range of acoustic/ultrasonic vibrations from 20 KHz-300 KHz, inclusive.

Partial discharge may cause a condition related to an operation of electric arcs such as familiar to an operation of "spark plugs" and other gapped devices. The instrument 1120 may be operable for detecting acoustic, sonic, ultrasonic, and electromagnetic noise related to PD. The monitoring of indications relating to the PD may detect early indication of possible insulation breakdown, which may reduce the dielectric strength of the fluid. Weakened dielectric strength of moist or contaminated fluid is associated with breakdown under electric fields with potential differences of below 25 kV. Compared with weakened dielectric strength, clean (uncontaminated) dry fluid may comprise dielectric strength sufficient to withstand electric fields at potentials in excess of 55 kV. Weakened dielectric strength may be associated with weakened mechanical strength properties of insulation. For example, a degree of polymerization of below 50 percent for insulation disposed between turns of the conductive coils is considered weak.

An embodiment may be implemented in which an off-axis detection may be used to locate a source of signals related to the detection of the PD. For example, an off-axis detection may be provided by installation of the instrument 1120 with the radiator 1050, and at least a second instrument with another (e.g., subsequent, or alternate-side-of the tank 1009) radiator bank.

Example Assembly of Instrument, Probe and Sensors.

Figure 12:
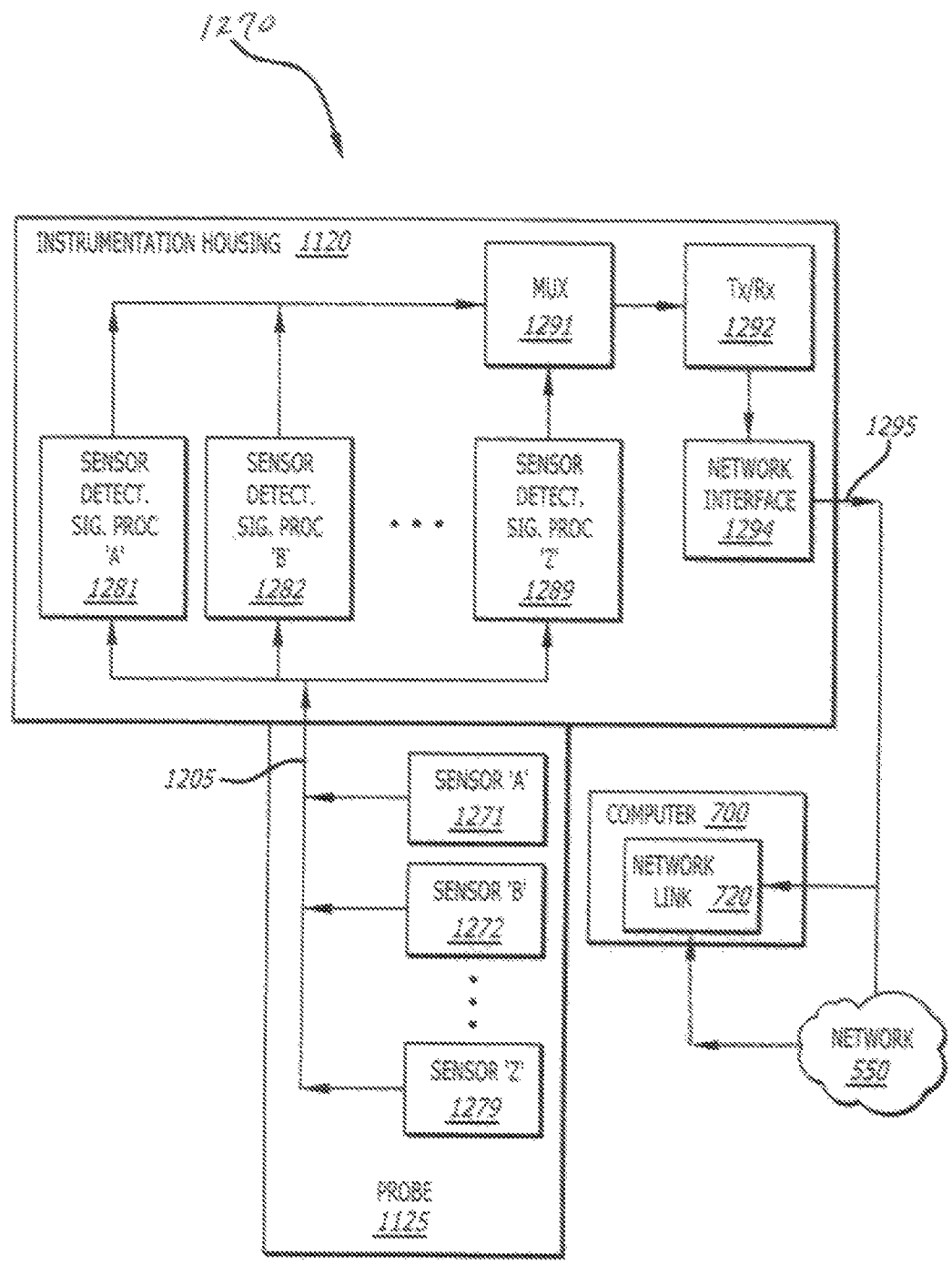
FIG. 12 depicts an example instrument, according to an embodiment of the present invention.

The probe 1125, including sensors installed therewith, and the instrument 1270 may be implemented as a composite instrumentation assembly, unitary instrumentation package, and/or matched component set ("assembly"). FIG. 12 depicts an example instrument, probe and sensor assembly 1270, according to an embodiment of the present invention. The assembly 1270 comprises the instrument 1120 and the probe 1125.

The probe 1125 comprises any number of sensors, each of which is operable for detecting one or more of the properties of the fluid 1151. The probe 1125 comprises at least a first sensor 'A' 1271. The probe 1125 may also comprise any additional number of sensors, represented in FIG. 12 with a sensor 'B' 1272, a sensor 'Z' 1279, etc. Each of the sensors may be operable for detecting distinct or different properties of the fluid 1151, relative to each of the other sensors. Additionally or alternatively, one or more of the sensors may be operable redundantly, e.g., for detecting one or more of the fluid properties detected with at least one of the other sensors.

A surface of the sensors, which is exposed to the flow of the fluid 1151, may be operational actively in relation to the detection of the chemical and/or physical fluid properties. One or more of the sensors may be disposed upon an outer surface of the probe 1125. For example, a surface of a sensor may conform, be configured to or mounted on (e.g., adaptively) a contour of an outer wall of the probe 1125. The sensors may be disposed in a configuration in which at least one actively operational surface of a sensor is exposed to, immersed in, and/or in contact with the flow of the fluid 1151, in which the probe 1125 is immersed, etc.

The probe 1125 may also (or alternatively) comprise an internal channel within an external enclosure of the probe. The channel is open to a portion of the flow of the fluid 1151. One or more of the sensors may be disposed within the channel. The sensors within the channel may be disposed in a configuration in which at least one actively operational surface ("active surface") of a sensor is exposed to, immersed in, and/or in contact with the fluid within the channel. For example, an outer active surface of a sensor may conform to a configuration of an inner wall of the channel, or the sensor may be mounted within the channel.

The sensors may comprise one or more microelectronic, opto-electronic, micro- and/or nano-scale electomechanical (e.g., MEMS) electrochemical, and/or detector components. One or more of the sensors may be operable for detecting the presence, identity and/or level of copper, silver, aluminum, and/or other metals, metal particles, metallic ions, ligands, etc. One or more of the sensors may be operable for detecting the presence, identity and/or level of hydrogen, oxygen and/or other dissolved or suspended gases. One of the sensors may be operable for detecting the presence and/or level of hydrocarbons. One or more of the sensors may be operable for detecting the presence, identity and/or level of products of combustion, arcing, and/or partial discharge. One or more of the sensors may be operable for detecting the presence, identity and/or level of moisture. One or more of the sensors may be operable for detecting the presence, identity and/or level of various contaminants. One or more of the sensors may be operable for detecting one or more physical properties of the fluid, such as conductivity level, dielectric strength (e.g., breakdown potential), IFT, viscosity, density, optical or spectrophotometric properties. One or more of the sensors may be operable for detecting a physical property of the fluid such as temperature and/or pressure. One or more of the sensors may be operable as described in the Watson, Roizman, and/or the Hedges or Voelker references.

An example embodiment may be implemented in which one or more of the sensors comprises a bead matrix. The sensor(s) may be operable for detecting the presence, identity, concentration and/or level of hydrogen and/or pressure. The sensors may be operable as described in one or more the Hedges or Voelker references.

Upon detecting the respective fluid properties, each of the sensors outputs a corresponding sensor detection signal. The sensor detection signals from each of the sensors is transmitted or conducted over one or more sensor detection signal channels 1205. The instrumentation housing 1120 comprises an array of detection signal processors, each of which is operable for accessing, amplifying, converting, evaluating, quantizing, scaling and/or packetizing ("processing") the detection signals 1205 from at least one of the sensors. For example, the instrumentation housing 1120 comprises at least a first sensor detection signal processor ('Detect. Sig. Proc.') 'A' 1281. The probe 1125 may also comprise any additional number of sensor detection signal processors, represented in FIG. 12 with a sensor detection signal processor 'B' 1282, a detection signal processor 'Z' 1289, etc.

The first sensor detection signal processor 'A' 1281 is operable for processing the sensor detection signal generated with the sensor 'A' 1271. The second sensor detection signal processor 'B' 1282 may be operable for processing the sensor detection signal generated with the sensor 'B' 1272, and the sensor detection signal processor 'Z' 1289 may be operable for processing the sensor detection signal generated with the sensor 'Z' 1279, etc. An example embodiment may thus be implemented in which each of the sensor detection signal processors A, B and Z, etc. are operable for processing a sensor detection signal generated by a corresponding one of the sensors A, B and Z, etc. An example embodiment may also (or alternatively) be implemented in which the instrumentation housing 1120 comprises at least one sensor detection signal processor operable for processing the sensor detection signals 1205 generated by two or more of the sensors.

One or more of the sensor detection signals 1205 may comprise a digital detection signal. One or more of the sensors may generate an analog sensor detection signal. The processing of the analog sensor detection signals may comprise, further, one or more operations related to analog to digital conversion (ADC). The ADC operations may be performed with the sensor, with a sensor detection signal processor corresponding to the one or more analog detection signal generating sensors, or partly in each.

Upon the processing of each of the sensor detection signals 1205, the sensor detection signal processors generate a corresponding processed detection signal. The processed detection signals comprise data, which characterize each of the detected fluid properties. The instrumentation within the housing 1120 may also comprise a multiplexer (MUX) 1291. The MUX 1291 is operable for multiplexing the processed detection signals from each of the sensor detection signal processors into an instrumentation signal. The instrumentation within the housing 1120 may also comprise a transmitter/receiver (Tx/Rx) 1292 and/or network interface 1294, which are operable for generating an instrument output signal 1295.

Figure 4:
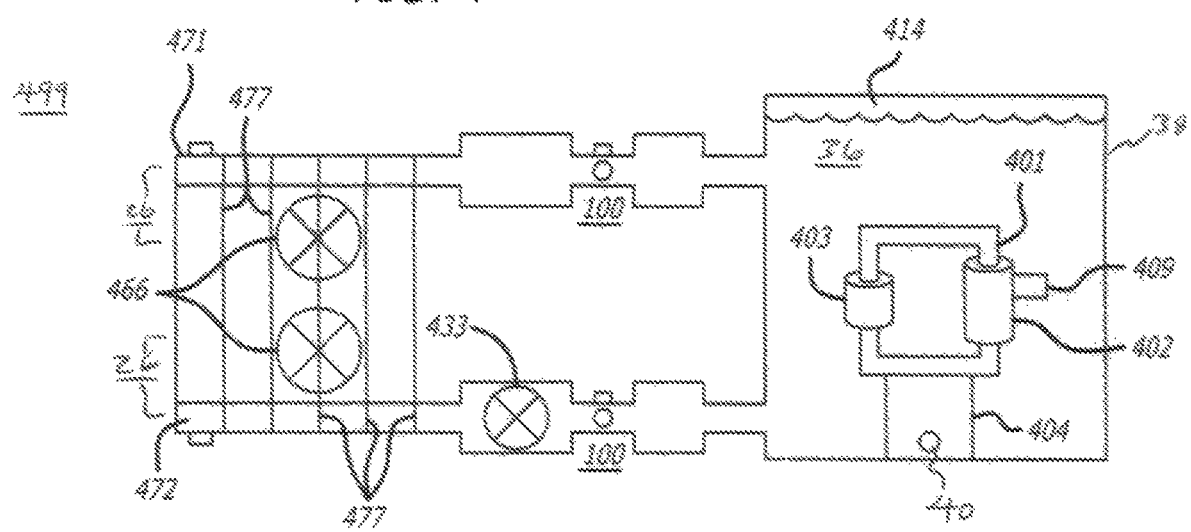
FIG. 4 depicts an example power device, according to an embodiment of the present invention.
Figure 7:
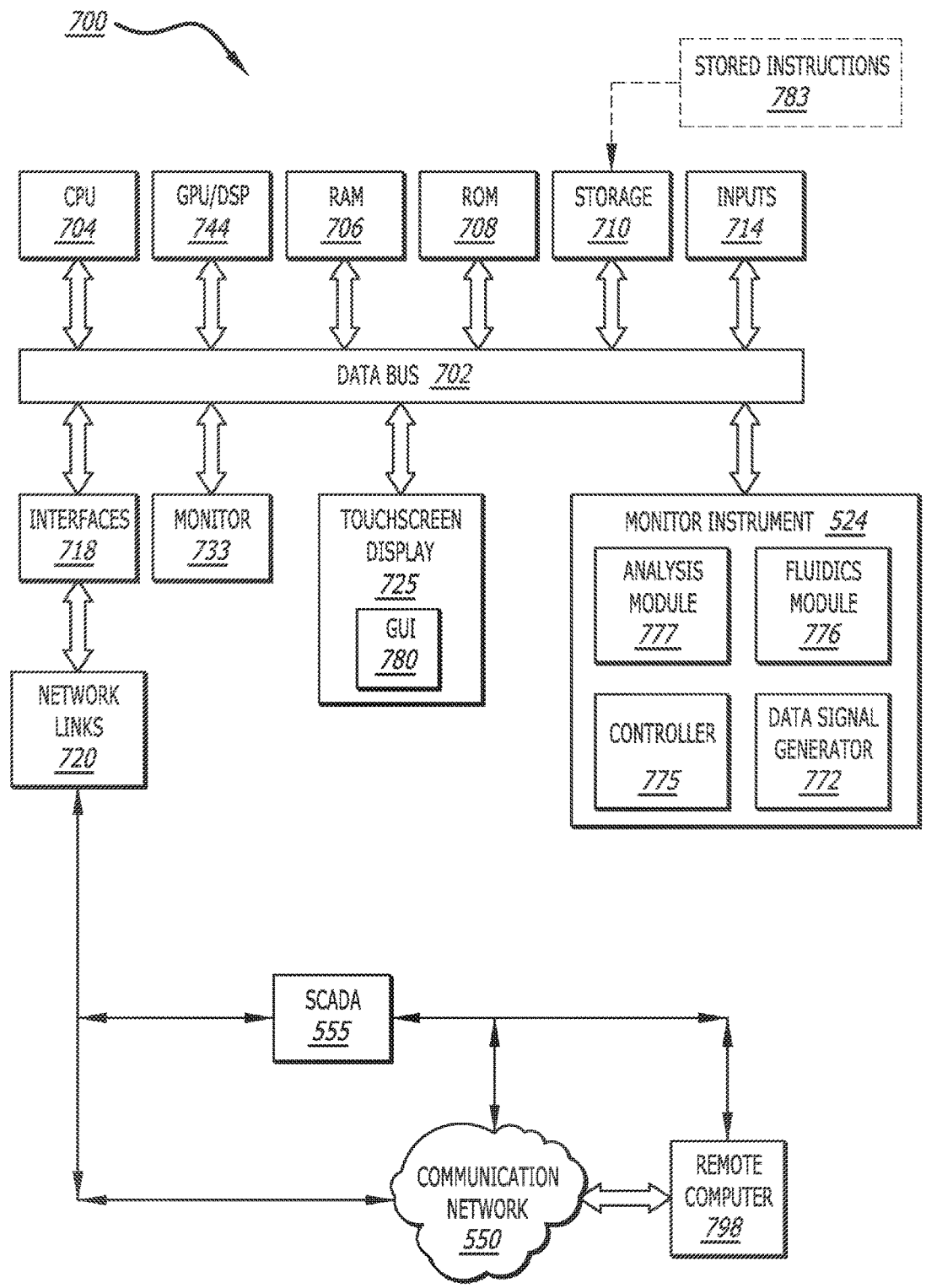
FIG. 7 depicts an example computer platform, according to an embodiment of the present invention

The output signal 1295 is conducted and/or transmitted, e.g., via the network 550 and the network links 720 to the computer 700 (FIG. 7). The computer 700 (e.g., monitor instrument 524, processors 704, 744, etc.) is operable for demultiplexing, evaluating, and processing the output signal 1295 in relation to the monitoring of the power device 400 (FIG. 4). The processing the output signal 1295 in relation to the monitoring of the power device 400 may comprise performing a process, executing a program, and/or computing an algorithm with the computer 700 (and/or the remote computer 798; FIG. 7). For example, the processing the output signal 1295 in relation to the monitoring of the power device 400 may comprise the computer 700 (and/or the computer 798) performing one or more of the process 80 (FIG. 8A) or the process 800 (FIG. 86), which are described below.

An example embodiment of the present invention relates to an instrument for monitoring an electrical power device. The instrument comprises a probe operable for detecting one or more properties of a fluid of the power device, each of the one or more fluid properties comprising at least one of a physical characteristic or a chemical characteristic of the fluid. The probe is disposed, removably, in contact with the fluid of the power device through a valve, with the valve disposed in an open position and mounted within a lateral envelope of a pipe through which a flow of the fluid is coupled longitudinally between a tank of the power device and a cooling device. The instrument also comprises a signal generator operable for generating a signal corresponding to each of the one or more detected properties. The probe may be operable for detecting at least two of the physical and/or chemical characteristics of the fluid.

The pipe is disposed between two sections of a header through which the fluid flows between the tank of the power device and the cooling device. The header comprises at least one of a lower header or an upper header, relative to each other, to a corresponding lower vertical position on the power device tank or the cooling device, and/or a corresponding upper vertical position on the power device tank and/or the cooling device.

An example embodiment of the present invention relates to a method for monitoring an electrical power device. The method comprises sensing a property of a fluid of the power device with one or more instruments. The one or more instruments each comprise a probe. The probes are placed, removably, into contact with the fluid through a valve, such as a ball valve. The valve is disposed in an open position and mounted within a lateral envelope of a pipe. The pipe is disposed in a header, through which a flow of the fluid is coupled longitudinally between a tank of the power device and a cooling device. A signal is generated based on the sensed property with the one or more instruments. Data related to the generated signal is exchanged with a network coupled communicatively with the one or more instruments. The exchanged data is processed in relation to the monitoring of the power device.

Example Power Transformer.

An example embodiment of the present invention relates to a power device, such as a transformer or reactor. FIG. 4 depicts an example power transformer 400, according to an embodiment of the present invention.

The insulating materials used in the power transformer 400 comprise fluids, such as oils or other nonconductive liquids of high dielectric strength. The core 401, a first coil 402, and at least a second coil 403 may be supported with a structural framework 404, immersed in (e.g., covered by; submerged within) the liquid insulation material 36 within a tank 38, and substantially separated (e.g., at least partially sealed) therein from an external environment 499 in which the transformer 400 is disposed. The insulating fluid 36 functions, further, to cool the internal components of the transformer 400 immersed therein.

The internal components immersed within the insulating liquid 36 comprise the core 401. The core is configured as a laminated array of sheets comprising a low reluctance material, such as iron or various alloys. The first conductive coil 402 is coupled, inductively, by the core 401 with the at least second coil 403. The insulating liquid 36 insulates the first coil 402 from the second coil 403, the first coil 402 and the second coil 403 from the core 401, and the individual windings of the first coil 402 and the at least second coil 403, at least in part, from other respective individual windings thereof. The individual windings of one or more of the coil 402 and/or the at least second coil 403 may be insulated, further, from other windings thereof by a solid coating or solid wrapping of another high dielectric strength material such as a paper, fiberglass, cloth, plastic, mica, or other natural, mineral, organic, and/or synthetic electrical insulation material. A load tap changer (LTC) 409 may be operable for changing the turns ratio of the coil 402 with respect to the coil 403 safely while the device 400 is under load.

During operation, significant heat may be generated by the internal components of the power transformer 400. The transformers used in generating stations, generation and transmission switchyards, and distribution substations, for example, may be rated to handle power at levels of hundreds, or even thousands of Megavolt Amperes (MVA), and associated with substantial internal heat production.

The heat produced by the internal transformer 400 components is transferred to the dielectric fluid 36 in which they are immersed. Within the transformer tank 38, the fluid 36 may flow about the components immersed therein by convection related to the heat transfer. One or more pumps 433 may add to the flow rate. The heat may be transferred from the fluid 36 to a heat sink. The heat sink may comprise the atmosphere 499.

A portion of the heat may be transferred to the atmosphere 499 by radiation and conduction from the external surface of the transformer tank 38, and associated heat radiating fins attached (e.g., welded) thereto. The heated fluid 36 may also flow through an array of cooling tubes 477. A significant portion of the heat may be transferred from the fluid 36 to the atmosphere 499 by conduction and radiation from the external surfaces of the tubes 477.

Fans 466, operable for promoting air flow about the exterior surfaces of the tubes 477, may increase the rate and/or amount of heat transfer. One or more fans 466 may be energized and deenergized switchably, and/or operable in relation to speed, under thermostatic and/or computer control. Thermostatic control, for example, may be responsive to temperatures of the transformer 400 and/or atmosphere 499.

Physical and chemical characteristics of the insulating fluid 36 within the power transformer 400 may change over time. The changes may relate to effects associated directly with the heating of the fluid 36, and with cycles or episodes of greater and lesser heating thereof. The changes may also relate to indirect heating effects, such as pressure variation within the tank 38.

Along with contemporaneous barometric variation characterizing the ambient atmosphere 499, the pressure variations within the tank 38 may correlate with venting of nitrogen (or other substantially inert gasses) blanketing the insulating fluid 36, and a possible ingress of air from the atmosphere 499. Oxygen within the air may oxidize a portion of the hydrocarbons and other organic material, which may comprise at least part of the insulating fluid.

An ingress of humid ambient air from the atmosphere 499 to the gas blanket 414 within the transformer tank 38 may also add moisture to the insulating fluid 36. The moisture may diminish dielectric strength and corresponding electrical insulating capability of the fluid 36. Moisture or other contaminants may also be released over time from solid insulation materials wrapped about the coils or from structural components. Moisture disposed within paper insulation, for example, may be released therefrom. Moreover, cellulose and/or other organic materials associated with the solid insulation wrapped about the coils (e.g., windings) of the core 402 and the core 403 may release moisture into the insulating fluid 36 by partial decomposition, which may be promoted by, e.g., heating and oxidation.

During the operation of the transformer 400 over time, various electrical transients may affect the characteristics of the fluid. Voltage transients, for example, may stress the fluid insulator 36, and the location and/or accumulation of the stresses may affect the insulating (and/or heat transfer) characteristics of the fluid 36 and promote conditions in which faults may occur.

While some faults may be associated with catastrophic effects, some other, "relatively minor" internal faults may not cause immediate, significant, substantial, or catastrophic failure of transformer operation. Such 'minor' internal faults, however, may be associated with significant changes to at least a portion of the insulating fluid 36.

Initially, the affected portion of the fluid 36 may be localized to a particular location within the transformer 400. As the fluid 36 flows through the transformer 400, however, the effects may, at least gradually, spread from an initial localization. Partial decomposition, oxidation, organic reactions, molecular polarization, carbonization, and other chemical changes within the fluid 36 may be caused or promoted. Such changes may affect, at least over time, the operational reliability of a power transformer.

The liquid insulating material with which the power transformer 400 is filled with thus provide electrical insulation for, and transfer heat from, an energized internal component such as the core 401, the first winding 402, and the at least second winding 403 (and any additional windings), also referred to herein as the "active parts" of the transformer 400. The liquid insulation 36 may comprise a mineral oil, synthetic oil, silicone based oils, vegetable oil, or other liquids that suitably meet dielectric, thermal, and chemical performance requirements. Mineral oils comprise the insulating fluid used in a significant portion of contemporary power transformers.

The fluid 36 is thus operable for providing electrical insulation of the components of the active part of the transformer 400, transferring heat therefrom, and helping to extinguish arcs, which may occur under some of the internal fault conditions that may occur. The fluid also dissolves gases generated associated with its partial degradation over time and operation of the transformer 400, moisture and gas from the solid (e.g., cellulose) insulation therein and its deterioration over time and operation, and gases and moisture the fluid 36 may be exposed to, such as ingress from the atmosphere 499.

An example embodiment of the present invention relates to monitoring the insulating fluid 36 for the presence, identity, and quantity of gases dissolved therein, and other properties and characteristics. The monitoring of the insulating fluid 36 may provide significant information relating to the condition, also referred to as the "health," of the transformer 400. The information provided by the monitoring may be processed in relation to detecting and characterizing trends indicative of the dielectric, heat transfer, and other physical and chemical condition of the fluid 36, and how the condition may be changing over time. An example embodiment may be implemented in which the monitoring is performed, at least in part, using one or more Dissolved Gas Analyzers (DGAs). Processing, examination, and interpretation of data provided by the DGAs may provide significant diagnostic value.

The volume of the fluid 36 is maintained within the tank 38 at a level sufficient to cover energized components of the active part of the transformer 400. The immersion of the energized components allows the fluid 36 to insulate them electrically from each other, and from ground potentials associated with the core 401 and the tank 38. The electrical insulation provided by the high dielectric strength characteristic of the fluid 36 inhibits formation and occurrence of internal electrical faults, and thus sustains the operation of the transformer 400.

The volume of the fluid 36 is maintained within the tank 38 at a level sufficient, further, to sustain the uninterrupted flow of the fluid 36 to the radiator tubes 477. The sustained uninterrupted flow of the fluid 36 through the radiator tubes 26 allows ongoing transfer of the heat energy produced by the active part of the transformer 400 from the radiators 26 to the atmospheric heat sink 499. The tubes may comprise components of a single radiator, or one or more stages of a multi-stage radiator unit, e.g., as described above. The flow of the fluid 36 thus removes heat from the active part of the transformer 400, which remains within a safe range of operating temperatures below a level at which thermal degradation or damage could occur.

Electrical energy transformation in the active part of the transformer 400 generates heat. The heat may result from resistive and reactive effects associated with current flow within the first winding 402 and the at least second winding 403, and inductive processes occurring within the core 401. The heat produced is transferred to the fluid 36 in which the active part of the transformer 400 is immersed. The heating of the fluid 36, and the subsequent cooling thereof, generates a convective fluid circulation through the tubes 477 of the radiator, which may comprise a single-stage or multi-stage radiator, e.g., as described above. Moreover, the fluid may also flow to one or more other single-stage or multi-stage radiators connected to the transformer tank, e.g., at a side opposite from a side to which a first radiator is attached. The one or more pumps 433 may mechanically augment the flow of the fluid 36.

Each radiator comprises an array of corrugated chambers or tubes 477, which are attached at one end to an upper header 471 and at an opposite end to a lower header 472 to form an effective manifold structure therewith. A surface of the manifold comprises a corrugated (or other) surface, over which the fluid 36 flows. The upper header 471 opens into an upper section of the tank 38, and is closed or sealed at an opposite end therefrom, or open to a subsequent cooling stage of a multi-stage radiator as described above. The lower header 472 opens into a lower section of the tank 38, and is closed or sealed at an opposite end therefrom, or open to a subsequent cooling stage of a multi-stage radiator as described above. Each of the sections of the single-stage (as depicted for example) or multi-stage radiator is operable to at least partially cool the transformer 400 by the transfer of heat from the heated coolant fluid 36 flowing through the tubes to the outside air of the ambient atmosphere 499. The heat exchange may be mechanically augmented an increase in the flow of the air across the radiators 26 by an operation of the fans 466.

The cooled portion of the fluid 36 in the lower portions of the radiator 26 has a higher density or weight, relative to the hotter liquid entering the upper header 471 and manifold. The cooled fluid 36 is pulled by gravity to the lower portion of the radiator 26 and the bottom header 471. The drop down of the denser cooled fluid 36 exerts a pulling force over the column of the fluid above it by a combination of thermal and siphon effects, referred to as a thermo-siphon effect. The column of the fluid 36 collects in the bottom header 471 of the radiator and flows back into the main tank 38, where it cools the active part of the transformer 400.

As the transformer 400 operates, the heat produced sustains promotion of the convection and associated siphon effects, and the fluid 36 continues to circulate. The flow rate of the fluid 36 may be affected by the amount of power transformed, and by the temperature of the atmosphere 499.

The radiators 26 may be installed fixedly, or in a removable configuration upon the tank 38. The radiators 26 may be installed fixedly onto the tank 38 during manufacturing and fabrication of the transformer 400. For example, the radiators 26 may be welded to the tank 38 during fabrication at a factory. The radiators 26 may be, alternatively, installed onto the tank 38 during assembly at the location of installation of a transformer. For example, the radiators 26 may comprise flanges installed at the open ends of the upper header 471 and the lower header 472.

The flanges of the radiators 26 may be bolted onto flanges attached, directly or indirectly, to the tank 38. The joints formed between the respective flanges may be sealed for liquid-tightness with an 'O-ring' or other suitable gasket. The gaskets comprise materials chemically suitable for use with the fluid and thermally suitable to remain liquid tight over the operating temperature range of the transformer and associated temperatures of the fluid 36. The installing of the radiators 26 onto the tank 38 may be associated with installation of other components, such as bushing insulators, associated with assembly of the transformer at the installation location. Upon assembly of the transformer, the tank 38 may be filled with the insulating fluid 36 and sealed.

The size and weight of the transformer, in relation to the availability of adequate shipping resources and the capability, capacity, passibility, and traffic associated with particular transportation routes and infrastructures, may be significant to the installation mode used for attaching the radiators 26 to the tank 38.

Removable sections of the radiator 26 are connected to the main tank 36 of the transformer 400 by the flanged joints. The top header 471 and the bottom header 472 thus form the manifolds with the radiator cooling chambers or tubes 477.

An example embodiment of the present invention may be implemented in which the radiator 26 comprises one or more removable sections. Each of the removable sections may be open to the flow of the fluid 36, or selectively isolated therefrom based on a respective corresponding position of a pair of valves. A first of the pair of valves is disposed to open or close, selectively, one of the removable radiator sections from the upper header 471. A second of the pair of valves is disposed to open or close, selectively, that removable radiator section from the lower header 472. Each of the valves may comprise a flapper valve. The flapper valve comprises an open position and a closed position. In the open position, the flapper valve allows the fluid 36 to flow through without significant obstruction. In the closed position, the flapper valve blocks the fluid 36 from flowing through. The removable section of the radiator 26 may be isolated by closing each of the corresponding pair of valves.

Upon the isolation of a particular section of the radiator 26, the fluid 36 remaining therein may be drained, and the section removed from the radiator 26 without further loss of fluid volume from the tank 38 and the transformer 400, at large.

The transformer 400 comprises a drain valve 40. The drain valve 40 is installed upon the tank 38 and disposed to allow draining of a significant portion of the liquid 36 therefrom and thus, from the transformer at large. The drain valve 40 may comprise a globe valve or a ball valve.

The globe valve comprises a body, a seat disposed within the body, and a disk disposed at the end of a threaded stem, which is disposed within a bonnet of the body. The disk may be moved vertically within a chamber of the body using manual rotation of the threaded stem, e.g., using a hand wheel as a torsional lever. In contrast to gate valves, the stem of the globe valve may not emerge to a substantial length from the bonnet. In the closed position, the disk is in contact with the seat to block the flow of the fluid 36. As the globe valve opens, the disk rises from the seat and allows the fluid 36 to flow through. The flow of the fluid 36 over a significant cross section of the globe valve is allowed by a serpentine contour associated with an area of the chamber of the body beneath the seat and disk.

With the valve in the open position, the opening provided by the lifting of the disk over the seat appears to span about half the height of the internal chamber of the valve body, e.g., as viewed from an open end.

The drain valve 40 may also provide access for sampling the liquid 36. Sampled specimens of the liquid 36 may be subject to electrical testing and chemical analysis. Data from the testing and analysis may relate to characteristics indicative of the condition of the fluid 36 and the transformer 400. Probes may also be used for obtaining these data. In some applications, the gathering of the data using the probes may be more convenient or timely than by the sampling of the fluid 36 through the drain valve 40. While the globe valves used in a significant number of contemporary and legacy power transformers accommodates flow of the full volume of the liquid 36 under its gate, its construction geometry may obstruct insertion of the probes.

Fittings may be added to the drain valve 40 to accommodate installing a sensor probe. However, the sensors installed through the fittings may be disposed within a pipe region associated therewith. The pipe region may be filled with a portion of the fluid 36 that, not circulating freely in the convection flow, may comprise a stagnancy. The stagnant sample with which the probe, immersed therein, is in contact may not fully or accurately characteristic of the greater portion of the fluid 36, which circulating more freely, is exposed to stirring and other mixing actions promoted by the convection.

In contrast to the globe valves, ball valves more freely allow accessibility of straight probes into the tank 38. It remains impracticable, however, to replace existing globe valve implementations of the drain valve 40 with ball valves. For example, risks exist in relation to sudden uncontrolled loss of a significant volume of the fluid 36 from the tank 38, concomitant environmental hazards and associated costs, and the resulting contemporaneous operational unavailability of the transformer 400, and further costs associated therewith.

As the transformer 400 operates over time, the electrical, thermal, mechanical, and chemical stresses to which the fluid 36 is exposed cause effects related to an expectable or predictable ("normal") degree of 'wear and tear' or deterioration. The normal wear and tear comprises a relatively gradual change in a general condition of the fluid 36 related to its continued serviceability as an electrical insulator and thermal coolant. The normal wear and tear may be exacerbated by additional electrical and thermal stresses, which may accompany sustained and/or repeated operation at or near design limitations, and/or faults or near-fault conditions that may occur. The changes are detectable using the sampling or probing, and analysis of the fluid 36. Changes detected in relation to gases dissolved in the fluid 36 may provide especially significant information.

The information provided may be significant to monitoring the overall health of the transformer 400. Thus, sample of the fluid 36 may be drawn from the fittings and ports in the drain valve 40. Other sample ports may also be installed at other positions disposed over the exterior vertical surfaces of the tank 38. The ports on the drain valve 40, however, may be too small to adequately flush the valve and associated pipe nipple connected to the tank 38, and ambient air may be drawn from the atmosphere 499 past threads on the pipe. The air may contaminate the sample, and/or introduce oxygen, moisture, and possibly other contaminants into the tank 38. The stagnant portions of the fluid 36 in the drain valve 40 and associated pipe nipple remain substantially dormant during operation.

Contaminants including moisture, microscopic stem packing particles, and other particles may collect and/or concentrate in the stagnant portion of the fluid 36 therein. The portion of the fluid 36 in this location can also be contaminated with hydrogen and other gases. The hydrogen may form when sun light illuminates and heats a side of the tank 38 on which the sample valve 40 is disposed. The solar heating may be exacerbated by heightened ambient temperatures that may characterize the installation location of the transformer 400, heightened temperature of the fluid 36 associated therewith and/or with heightened operational power levels, all of which may combine to increase the rate of hydrogen gas production. The hydrogen gas produced in this area of the tank 38 is soluble in the stagnant portion of the fluid 36 pooled proximate thereto, and may remain therein until a sample is drawn.

The stagnant pooling of the liquid 36 near the bottom of the main tank 38 during normal operation allows the accumulation of sludge, contaminants, moisture, and debris. The accumulation may be accentuated near the lowest parts of the main tank 38, e.g., proximate to the main drain valve 40.

The globe valves of some implementations of the main drain 40 may comprise brass. The tank 38 may comprise steel. The brass valve is installed into electrolytic contact with the steel case 38, and disposed within humidity characteristic of the atmosphere 499, sufficient moisture may be present to allow galvanic action to promote the flow of circulating currents between the dissimilar metals. This effect too may generate hydrogen gas, which may accumulate in the stagnant portion of the liquid 36 in the vicinity of the drain valve 40. Without thorough flushing of the drain valve 40, probes and samples may sense the accumulated hydrogen and indicate a high concentration thereof, which may be mistakenly interpreted to represent actual conditions within the greater circulating portion of the fluid 36.

Prior to taking an oil sample therefore, flushing is used to remove the potentially contaminated stagnant portion of the fluid 36 from the area of the drain valve 40. A cleaner sample, more accurately representative of the condition of the substantial volume of the fluid 36 within the case 38, may thus be obtained.

Once drawn, the samples of the fluid 36 may be subjected to laboratory analysis. In addition to electrical testing related to its present dielectric strength, hydraulic and other physical properties, such as interfacial tension (IFT), viscosity, density and specific gravity, may be measured against baseline and/or threshold values, as well as results obtained by earlier testing. Trending may be observed and evaluated in relation to changes in properties that may indicate aging, wear and tear, and more serious deterioration of the fluid 36. Gas analysis may be performed on the samples of the fluid 36. Dissolved gas analysis (DGA) helps to characterize the fluid 36 chemically, and provide indication therefrom related to the general, overall health of the transformer 400, and to existing, developing, or improving conditions that may be associated with, and characteristic of faults. Gas chromatography may be performed on the samples, which may also be subjected to infrared (IR) and mass spectroscopy, and other analytics such as nuclear magnetic resonance (NMR) and Ramen spectroscopy. Gas analysis may be performed on the samples of the fluid 36. Dissolved gas analysis (DGA) helps to characterize the fluid 36 chemically, and provide indication therefrom related to the general, overall health of the transformer 400, and to existing, developing, or improving conditions that may be associated with, and characteristic of faults. Gas chromatography may be performed on the samples, which may also be subjected to infrared (IR) and mass spectroscopy, and other analytics such as nuclear magnetic resonance (NMR) and Ramen spectroscopy.

Various and variable latencies may sometimes be associated with shipping, transport, handling, and accounting for the source and identity of the samples, at laboratory locations remote from that of the installation of the transformer 400. Errors associated with the handling and accounting for the source and identity of the samples may also sometimes occur, as well as loss, damage, or contamination of the samples during the shipping, transport, and handling.

One or more sensors may be installed in contact with the fluid 36 to monitor its condition continuously, or repeatedly over various programmable periods of time. Data gathered by the sensor from the fluid 36 may be stored and processed with memory, microprocessors, and other integrated circuit (IC) components of an instrumentation package associated with the sensor. These data may be communicated by transceiver related components of the sensor instrumentation package, via a SCADA system and/or data network, for storage, processing and analysis with a database.

The database may be associated, for example, with an electrical utility (or other entity) having cognizance over the operation and maintenance of the transformer 400. The data may also be communicated via one or more radio frequency (RF) channels, telephonically, coaxially, and/or optically via one or more packet switched data networks. The data networks may comprise the Internet, a secure internetwork, 'internet of things' (IOT), and/or "cloud" based storage, transport, processing, and analysis infrastructure. The data may be communicated using one or more networking protocols, such as Transport Control Protocol/Internet Protocol (TCP/IP). The data may be encrypted for transmission, and handled using any of various data security techniques.

The use of the sensors to continuously monitor the fluid 36 may indeed avoid the latency and errors, etc. sometimes associated with the remote-site laboratory analysis. However, the installation of the sensors may be constrained in relation to some transformers by the number, size, placement, and type of valve-regulated openings into which probe components of the sensors may be inserted. One or more valve covered accesses may be installed atop of the tank 38, but their size may not suffice to accommodate insertion of the sensors. While the two inch dimension characteristic of the main drain valve 40 may suffice, its opening is nonetheless restrictive, and its location on the tank 38 is not ideal for contact with other than the stagnant and possibly contaminated portion of the fluid 36.

The probes installed on some sensors may be accommodated by the two inch opening of the drain valve 40, for accessing the fluid 36. These probes may be attached directly to an instrumentation body of the sensor. However, the sensor instrument body may not clear a surface of the ground plane adequately at the location of the drain valve 40 because of its proximity to the ground plane at the bottom of the tank 38. Pipe plumbing may be added to offset for clearance of the instrument body.

Some DGA instruments "pull in" a fresh sample of the fluid 36 from the drain valve 40 and, upon performance of its sensing operations, pump the sample portion back to the same area, again, at which significantly less flow of the fluid 36 occurs, relative to the main convective flow thereof. Cross-contamination, in which the first sampled portion of the fluid 36 is placed back in the same vicinity of the sampling probe and affects the next or other subsequent sample near the drain valve 40, may be avoided by the action of some sensors. For example, some nine-gas online sensors return the just-monitored sample of the fluid 36 back to the tank 38 via relatively longer return lines, to an area of the tank 38 separated from the pick-up area, to an unused opening, and thus avoid re-sampling, at least partially, some of the same portion of the liquid 36 at the next or subsequent monitoring time.

Implemented as a two inch globe valve, the drain valve 40 may restrict, at least to some degree, the access of sensors through the chamber within its body, is disposed on the tank 38 at a low point possibly associated with a stagnant pooling of the liquid 36 and accumulation of contaminants. Some smaller, inexpensive, and/or "online" sensors may be installed in association with what valve covered openings may be disposed over the surfaces of the tank 38 on some transformers, if any. Some larger sensor devices may provide more capability, versatility, sensitivity, accuracy, and/or reliability than the smaller, cheaper, etc., but the access thereof for the monitoring of the fluid 36 may be limited, or at least directed through the drain valve 40, which may be at least partially restricted.

Example embodiments of the present invention relate to the use of various sensors for monitoring the fluid 36. Each of the sensors comprises one or more sensing and analytic capabilities in relation to monitoring one or more of a plurality of chemical (e.g., DGA) and physical (e.g., dielectric, hydraulic, thermal) characteristics of the fluid 36. Each of the sensors, further, may be disposed within a configuration selectable from among a range of sizes, form factors, contours, shapes, materials, durability ratings, environmental certifications, and/or packages.

Example Tubular Assemblies.

Figure 2:
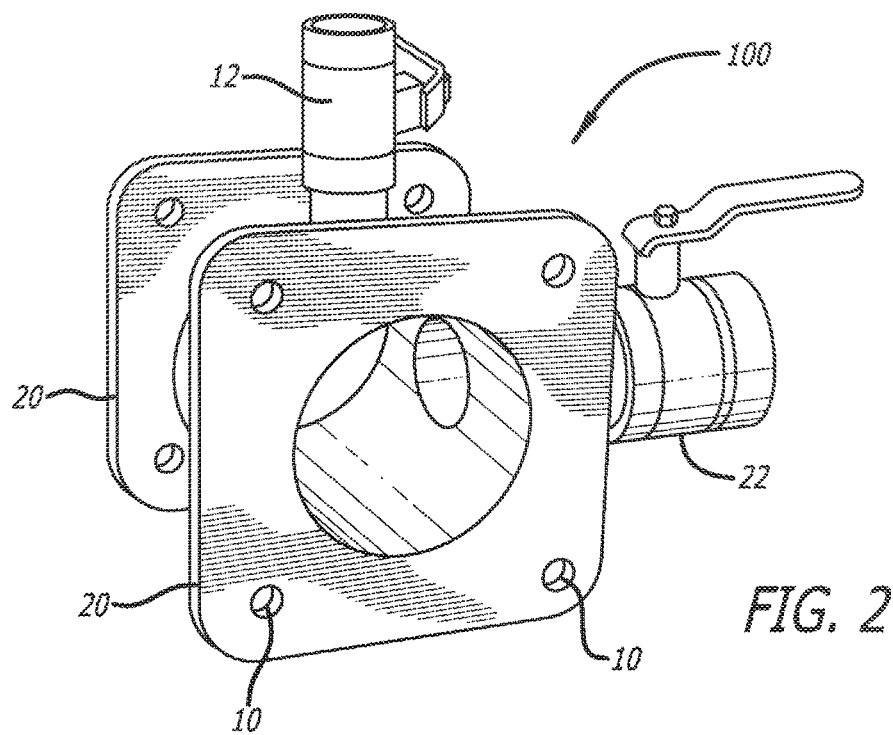
FIG. 2 depicts the example tubular assembly from a second view, according to an embodiment of the present invention.

In an example embodiment of the present invention, the radiator header 471 and the radiator header 472 each comprise a tubular assembly disposed between a removable section of the radiator 26 and the main tank 38 of the liquid filled power transformer 400. FIG. 1 depicts a first view of an example tubular assembly 100, according to an embodiment of the present invention. The tubular assembly 100 is shown in the first view from a vertical perspective of a first lateral end. FIG. 2 depicts a second view of the example tubular assembly 100, according to an embodiment of the present invention. The tubular assembly 100 is shown in the second view from a more horizontal perspective of the first lateral end, relative to the first view.

The first view shows the double flanged tubular assembly 100 with welded fittings and threaded pipe fittings 14 and close-nipples 18, to accommodate large size ball valve 22 and small size ball valve 12. The second view shows the interior of the tubular assembly, from which fresh flowing samples of the fluid 36 may be accessed by probes and monitored.

Figure 3:
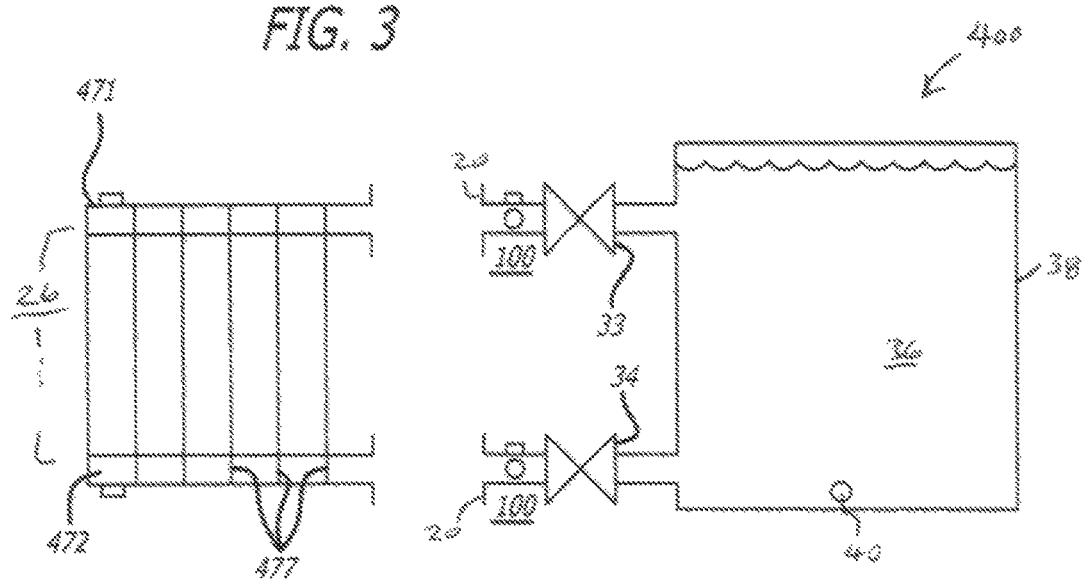
FIG. 3 depicts the example tubular assembly installed with a transformer, according to an embodiment of the present invention.

FIG. 3 depicts the example tubular assemblies 100 installed with the transformer 400, according to an embodiment of the present invention. One of the tubular assemblies 100 is installed between the flanges of an upper flapper valve 33 installed proximate to the tank 38 and the upper header 471. One of the tubular assemblies 100 is installed between the flanges of a lower flapper valve 34 installed proximate to the tank 38 and the lower header 472.

The tubular assembly 100 comprises a section of tubing 111 disposed longitudinally between a pair of transverse flanges 20. The flanges 20 may be attached fixedly (e.g., welded, brazed) to the tubular section 111. Each of the flanges 20 may comprise a material similar to (or compatible with) that of the tubular section 111. Each of the flanges 20 may comprise a plurality of penetrations 10. Each of the flanges 20 may be fastened (e.g., bolted) to, and sealed (e.g., gasketed) in contact with a complimentary flange associated with the upper header 471 or the lower header 472, and fastened thereto by a fastener (e.g., bolt) inserted through the penetrations 10 and fixed (e.g., with a nut).

The tubing section 111 may comprise an inner diameter that matches an inner diameter of the upper header 471 and/or the bottom header 472. The tubing section 111 may comprise an outer diameter that matches an outer diameter of the upper header 471 and/or the bottom header 472. A thickness of the tubing section 111 may match a thickness of the upper header 471 and/or the bottom header 472. The tubing section 111 may comprise a material that matches a material of the upper header 471 and/or the bottom header 472.

An example embodiment may be implemented in which the tubular assembly contains a plurality of access ports. The access ports may comprise pipe thread fittings. The pipe thread fittings may accommodate one or more ball valves. Each of the ball valves may comprise a size distinct from one or more of the other ball valves.

In an example embodiment of the present invention, the liquid filled power transformer 400 comprises the tank 38, the main drain valve 40, and a plurality of ports disposed upon a surface of the tank 38. The fluid 36 may be sampled through the ports. An example embodiment may be implemented in which four or more of the sampling ports are disposed at locations on the surface of the tank 38 remote from, or at least translated vertically and/or horizontally in relation to the drain valve 40.

Example embodiments may thus provide sampling access at levels above the level of the ground plane of the transformer 400 and associated with the drain valve 40, with related ergonomics related to sampling the fluid 36. Further, the heights at which the sampling ports may be accessed may reduce the length, contour, and/or configuration of offset plumbing pipe used for coupling instrumentation or sampling chambers, relative to ground level and the vicinity of the drain valve 40.

In an example embodiment of the present invention, the liquid filled power transformer 400 comprises one or more instruments coupled to the tank 38 and operable for sampling and/or monitoring the fluid 36 in relation to one or more chemical or physical characteristics thereof. The transformer 400 also comprises a plurality of threaded pipe fittings. Each of the threaded pipe fittings comprises a different size of one or more of an inner and/or outer diameter of threaded pipe, or a dimension and/or pitch of a threading associated therewith. Each of the instruments is coupled to the transformer 400 in relation to the sampling and/or monitoring of the fluid 36 by at least one of the threaded pipe fittings.

Each of the instruments may comprise one or more probes. In an example embodiment of the present invention, the transformer 400 comprises one or more ball valves. The instrument probes, and/or sample probes, may be placed into direct access with the fluid 36 through the ball valves. The instrument and/or sampling probes may comprise a straight configuration, which accesses the fluid 36 through the ball valves. The probes may be placed into contact with the convective flow of the fluid 36 via the ball valves.

In an example embodiment of the present invention, sampled fluid may be returned into a moving (e.g., convective) flow of the fluid 36. Thus, the returned post-sample fluid is mixed into the bulk of the fluid 36, which avoids stagnation and the possibility of influencing subsequent sampling.

In an example embodiment of the present invention, the instruments comprise a multi-gas sensitive dissolved gas analyzer (DGA). Long sampling lines for coupling the multi-gas DGA to the source of the fluid 36 or the top of the tank 38 is obviated by coupling to a nearby access port to the adjacent ball valve located on the header tube assembly. The risk of cross-contamination of subsequent samples of the fluid 36 is thus reduced.

The ball valves may comprise brass and/or stainless steel ball valves, and the sample ports may comprise stainless steel close-nipples. Example embodiments of the present invention may thus be implemented, which avoid generation of circulating currents, galvanic action between dissimilar metals, and related production of hydrogen gas and inaccuracy introduced therewith in results of the DGA monitoring of the fluid 36. An attachment tab may be associated with each of the ball valves for connecting a safety lanyard. The safety lanyard and attachment tab deter the ejection of probes under hydraulic pressure exerted by the fluid 36 in the presence of an untightened gland nut associated with the probe.

The monitoring of the fluid 36 may comprise a measurement of a moisture content, a pressure, and a temperature thereof at the upper header 471 and at the lower header 472. A differential pressure between a volume or portion of the fluid contained within the upper header 471 and a volume or portion of the fluid contained within the lower header 472 may also thus be measured. A hysteresis may computed related to the measured moisture content. The computed hysteresis allows monitoring of a dynamic movement of the moisture between the fluid 36 and paper and/or other cellulose containing solid dielectric material within the transformer 400. The movement of the moisture between the paper insulation and the fluid 36 may relate to the loading of the transformer 400 over time.

An example embodiment of the present invention may be implemented in which the monitoring of the moisture content, the pressure, and the temperature of the fluid 36, the differential pressure between a volume or portion of the fluid contained within the upper header 471 and a volume or portion of the fluid contained within the lower header 472, and/or the computation of the moisture related hysteresis is performed as described in Roizman, which is incorporated by reference for all purposes in its entirety.

Multiple locations are provided for sampling and/or monitoring the fluid 36. The probes may be fully inserted directly into a fresh moving stream of the fluid 36, which may avoid inaccurate results related to stagnancy. The above ground sampling/monitoring locations provide ergonomic convenience and obviate the use of offset plumbing. Ball valves of various sizes allow installation of a plurality of sensors, each of which may be distinct in size and configuration from one or more of the others. Embodiments of the present invention thus relate to a plurality of analytic and diagnostic tests and online monitoring of the fluid 36.

The proximity of fresh flowing portions of the fluid 36 allows reduction in the length of lines for returning the samples after analysis with multi-gas spectrometers and/or other instruments to the transformer 400. The installation of the tubular assembly 100 into the upper header 471 and into the lower header 472 allows full access to sensors operable for detecting and measuring the change in temperature when the fluid 36 is cooled upon passage through the radiator 26. Embodiments of the present invention thus permit measurement of the dynamic state of moisture content in the fluid 36 and provide information related to the aging and condition of the solid paper insulation. Such information is significant for monitoring the operational health of older transformers. With newer transformers, the information may be monitored over the drying out vapor phase, which allows more accurate determination of when the transformer has reached a minimum moisture level, reduced related energy costs, and increased production time.

Example Installation Process.

In an example embodiment of the present invention, the tubular assembly 100 is installed between the removable radiator section 26 of the liquid filled power transformer 400, and the main tank 38 thereof. Upon deenergizing the transformer 400, the flapper valve 33 and the flapper valve 34 may be closed and locked. A portion of the fluid 36 may thus be isolated within the valved- off section of the radiator 26. A greater portion of the fluid 36 remains within the tank 38. The portion of the fluid 36 isolated within the valved off section of the radiator 26 may be drained therefrom by opening the drain pipe plug installed with the lower header 472, and a vent pipe plug installed with the upper header 471.

The drained section of the radiator 26 may be unbolted and removed temporarily. Upon servicing the surface of the flanges from which the radiator section was removed, new gaskets, O-rings or other seals may be applied thereto, and a pair of the tubular assemblies 100 may be installed. The flanges of one end of each of the tubular assemblies 100 is bolted to a corresponding one of the flanges from which the radiator section was removed. Upon servicing the surface of its flanges and application of new gaskets, O-rings or other seals, the removed section of the radiator 26 may then be reinstalled. The flanges of the other end of each of the tubular assemblies is bolted to a corresponding one of the flanges of the section of the radiator 26.

Upon inspecting each of the joined flanges and seals, the bolts with which they are fastened may be tightened to a specified torque value. The ball valves of each of the tubular assemblies 100 are closed (or checked to be closed). The radiator drain plug is reinstalled into the lower header 472 and closed. The lower flapper valve 34 may then be opened to allow each of the tubular assemblies 100, and the reinstalled section of the radiator 26 to refill with the fluid 36 from the tank 38 (and/or with a fresh supply of the fluid 36). The radiator vent plug is kept open to release air as the fluid 36 fills each of the tubular assemblies 100 and refills the reinstalled section of the radiator 26. The radiator drain plug may be partially reopened to purge a small amount of the fluid 36, upon which it is shut, and possibly torqued. Upon totally filling each of the tubular assemblies 100 and refilling the reinstalled section of the radiator 26, the fluid 36 displaces all of the air therefrom, and a small amount of the fluid 36 may be observed to emerge from the radiator vent plug. The radiator vent plug may then be closed to seal the upper header 471.

The upper flapper valve 33 may then be opened, and pressure of the fluid 36 balanced between the tank 38 and the reinstalled section of the radiator 26. With the flapper valve 33 and the flapper valve 34 both open, the fluid 36 may flow freely between the tank 38 and the radiator 26, and the convection cycle reestablished. Upon completion of electrical testing and other maintenance that may have been conducted contemporaneously with the installation of the pair of the tubular assemblies 100, the transformer 400 may then be placed back in operation.

With each of the tubular assemblies 100 thus installed, four or more additional oil sampling locations are provided for sampling and/or monitoring the fluid 36. Various types, sizes, and configurations of instrument probes may be accommodated by the sampling/monitoring locations of the tubular assemblies 100, and online monitoring sensors, probes or instrument components installed therewith in a fresh-flowing and non-stagnant portion of the convective stream of the fluid 36 during the operation of the transformer 400. Characteristics, properties, conditions, and parameters associated with the fluid 36 including, for example, temperatures, pressures, moisture content, presence, identity, and levels of dissolved gases, and hydraulic and thermal factors may all be monitored in convenient, safe, accessible locations.

Example embodiments of the present invention relate to providing access for probes and sensors of various types, sizes and configurations, including straight configurations, into the convective flow of the fluid 36, and obviate the use of the main drain valve 40 for the installation of probes for the sampling/monitoring.

At present, the average age of liquid filled power transformers in service in the United States is about 46 years old; exceeding their intended operational 30 year life span by over 50%. Over time, gaskets and other seals with which the supply of the fluid 36 is retained within the transformer sustain wear due to chemical and mechanical stresses. For example, ultraviolet (UV) light to which the seals are exposed advance wear thereof due to weathering effects. The worn seals may leak. The leakage of the worn seals may allow the ingress of moisture from the ambient atmosphere 499.

The moisture raises the moisture content of the fluid 36 and may be absorbed into the solid dielectrics of the transformer, such as the paper insulation wrapped around the coils of the first winding 401 and the at least second winding 402. The moisture absorbed into the solid dielectrics may compromise the quality or strength of the electrical insulation provided therewith. Moreover, the paper, and other cellulose related solid insulation, may deteriorate over time and release additional moisture. The deterioration may be accelerated and/or exacerbated by electrical stresses presented in high voltage environments, faults and near-fault conditions, and cycles or other episodes of heating and cooling corresponding to various operating states and loads experienced by the transformer.

The moisture content of the fluid 36 is related directly to the occurrence of electrical faults and operational failures of transformers. Moreover, transformer life extension may comprise a significant factor in sustaining the reliability of the American electrical infrastructure in general, and may become more significant during times of economic stress and reduced infrastructure development.

Moisture may migrate in and out of the fluid 36 from the paper and other solid insulation components on a periodic, even daily basis, due to the heat sustained and produced by the transformer 400. At relatively low loadings and associated temperatures for example, the moisture may remain within the paper or other solid dielectric materials. As the transformer is loaded, greater amounts of heat are generated within the active area thereof, and moisture may migrate out of the paper and into the fluid 36. Such migration of the moisture in and out of the fluid 36 and the solid insulation material exhibits a hysteresis in transition, sometimes referred to as a "cloud" effect (based on graphic appearances of related plots).

An example embodiment relates to a process for tracking the moisture related hysteresis. The process may comprise computing a "moisture cloud." The computation comprises measuring a temperature differential between the portion of the fluid 36 within the upper header 471, and the portion of the fluid 36 within the lower header 472. Temperature probes, moisture probes, and/or pressure probes may be immersed within the upper header 471 and within the lower header 472. Information collected with at least a pair of the pressure probes may relate to measuring and/or monitoring a differential pressure between a volume or portion of the fluid contained and/or flowing within the upper header 471 and a volume or portion of the fluid contained and/or flowing within the lower header 472. Instrumentation may be informed with data collected with the sensors. Computation of the moisture cloud provides an indication of the degree of the migration of the moisture, with which the health of the transformer may be monitored in general, and the dielectric condition of the fluid 36 monitored more particularly.

Example embodiments of the present invention relate to the full access of the moisture, pressure, temperature probes, and the differential pressure probes, into contact with (e.g., immersion within) the freely flowing stream of the fluid 36. The accurate determination of the moisture content, and corresponding temperature thereof is significant to determining the condition of the fluid 36, and planning of proactive maintenance, e.g., in older transformers. With newer transformers, the evaluation of the moisture condition, e.g., during dry-out in the vapor-phase, allows an accurate assessment of as-built conditions, and establishment of significant benchmarks related to Factory Acceptance Testing (FAT).

The accurate benchmarking of the moisture levels may inform transformer manufacturers in relation to adequate, effective dry-out terminations, with potential savings related to production energy costs. Example embodiments of the present invention may thus comprise a component of an original equipment manufacturing (OEM) specification set forth by a purchaser of transformers and related equipment. An example embodiment of the present invention relates to an instrumentation system operable for monitoring the fluid 36 continuously in real time.

Example Transformer Instrumentation System.

Figure 5:
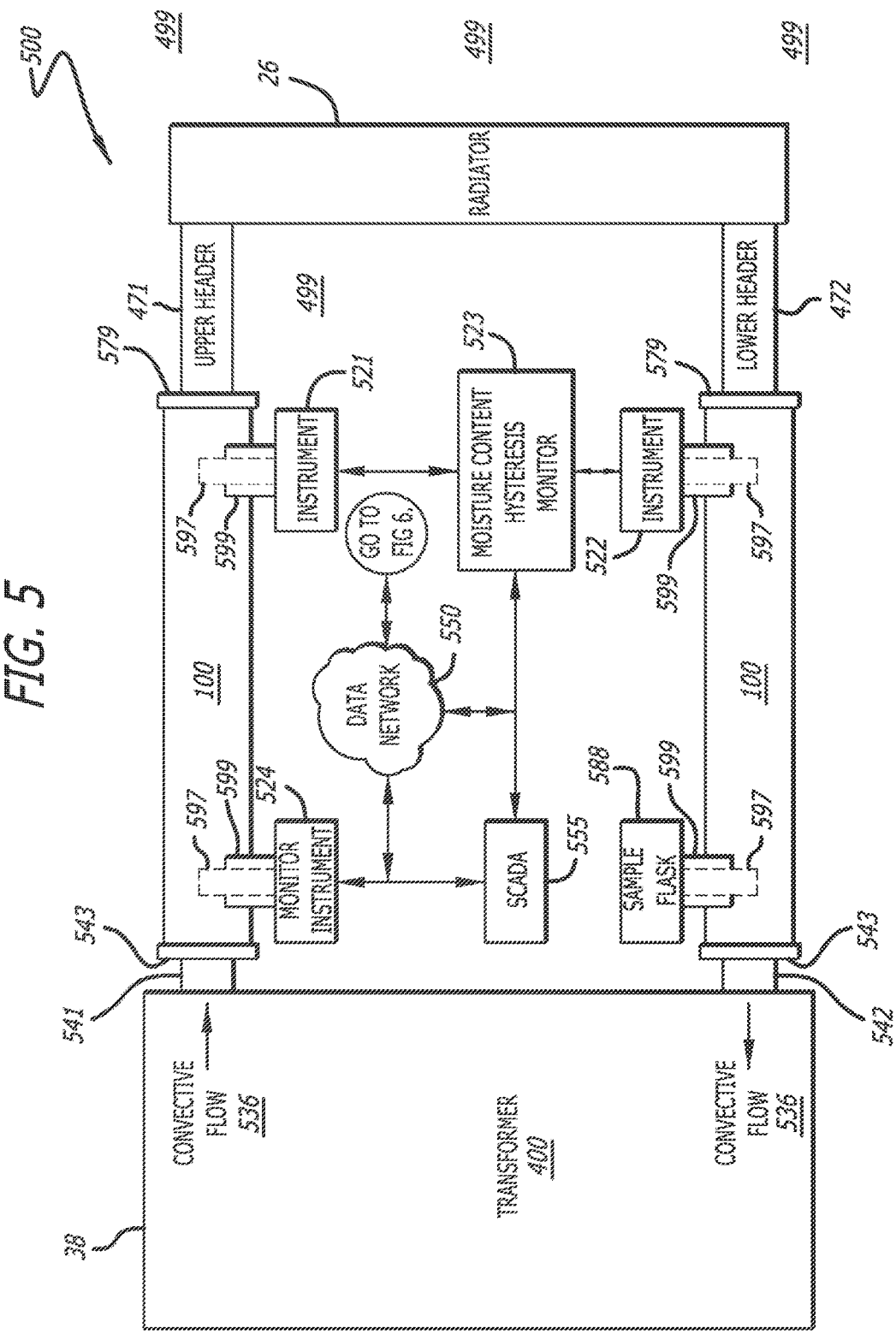
FIG. 5 depicts an example transformer instrumentation system, according to an embodiment of the present invention.

FIG. 5 depicts an example transformer instrumentation system 500, according to an embodiment of the present invention. The instrumentation system 500 comprises at least a pair of the tubular assemblies 100. A first of the pair of tubular assemblies 100 is fastened by a first of its flanges to a sealed flange 543 on an upper outlet 541 of the tank 38 of the transformer 400, and by the second of its flanges (opposite to the first) to a sealed flange 579 of the upper header 471 of the radiator 26. A second of the pair of the tubular assemblies 100 is fastened by a first of its flanges to a sealed flange 543 on a lower outlet 542 of the tank 38 of the transformer 400, and by the second of its flanges (opposite to the first) to another sealed flange 579, on the lower header 472 of the radiator 26.

The fluid 36, heated within the tank 38 during the operation of the transformer 400 flows in a convective current 536 flows out the upper outlet 541, through the first of the tubular assemblies 100, and the upper header 471, into the radiator 26. Cooled by heat transfer from the radiator 26 to the atmospheric heat sink 499, the fluid 36 flows in the convective current 536 through the lower header 472, and the second of the tubular assemblies 100, and returns to the transformer 400 through the lower outlet 542 of the tank 38, where it may be reheated. The reheating of the fluid 36 within the transformer 400 sustains the convective circulation flow 536 through the instrumentation system 500.

The instrumentation system 500 comprises at least one monitor instrument 524. A probe and/or sensor 597 associated with the monitor instrument 524 is placed into thermal, hydraulic, and/or other physical contact with the convective flow 536 of the fluid 36, and/or immersed at least partially therein through one of the ball valves 599 of at least one of the tubular assemblies 100. The probe/sensor 597 is operable for sensing a characteristic property of the fluid 36, generating a signal corresponding to the sensed characteristic, and communicating or providing the generated signal to the monitor instrument 524.

An example embodiment of the present invention may be implemented in which the probe/sensor 597 is operable, further, for performing one or more analytic and/or diagnostic tests on the sampled portion of the fluid 36, with which it is in contact. The signals corresponding to the characteristic property of the fluid 36 may generated by the sensor/probe 597 based on the analytic/diagnostic tests performed therewith. The monitor instrument 524 is operable for processing the signals provided by or communicated from the sensor/probe 597, and generating corresponding data signals, for communicating to a SCADA system 555 and/or over a data network 550.

The probe/sensor 597 may be, alternatively or additionally, operable for sampling a portion of the fluid 36, and for providing the sample fluid portion to the monitor instrument 524 and returning the sample fluid portion therefrom to the convective current flow 536. An example embodiment of the present invention may be implemented in which the monitor instrument 524 is operable for performing one or more of the analytic and/or diagnostic tests on the sampled portion of the fluid 36 provided thereto by the probe 597, and for generating at least some of the signals corresponding thereto.

In an example embodiment, the at least one monitor instrument 524 is coupled communicatively to a SCADA system 555, and/or a data network 550. The monitor instrument 594 is operable, further, for providing the data signals based on the processed signals to the SCADA system 555 and/or data network 550.

Figure 6:
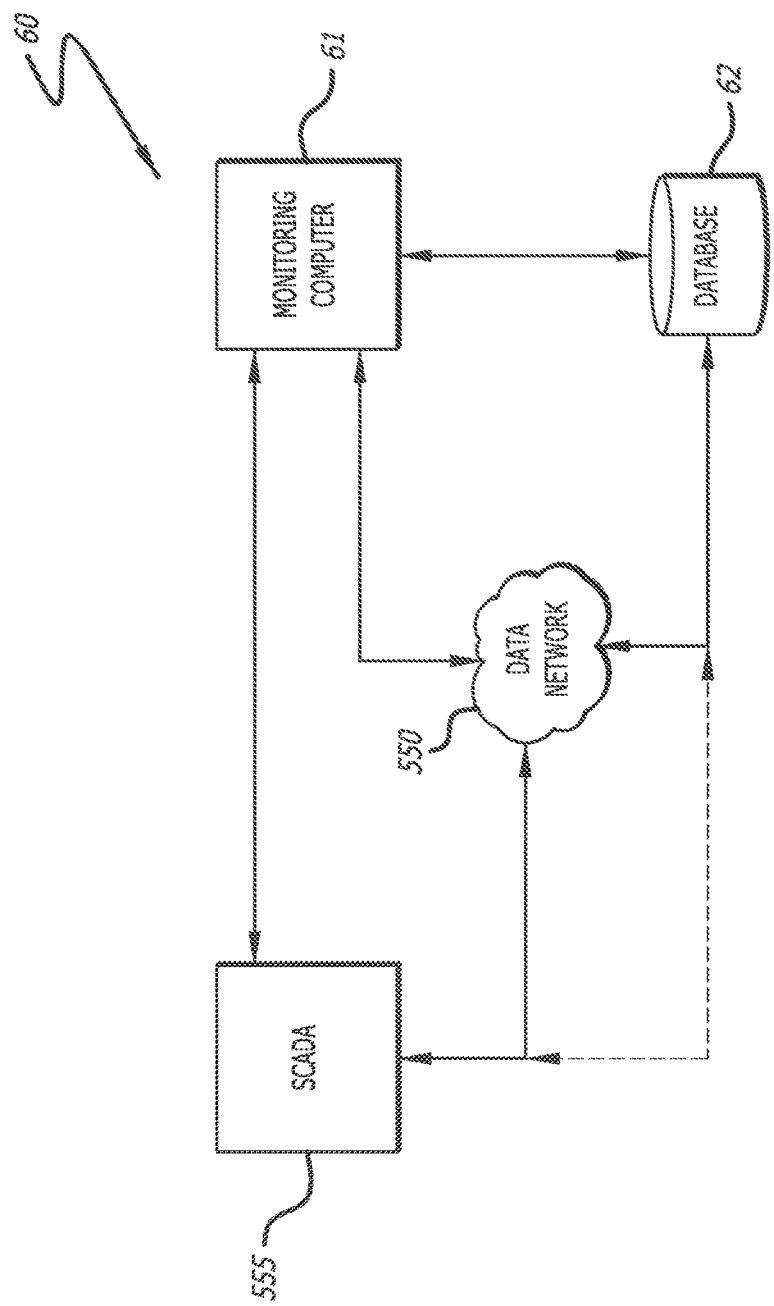
FIG. 6 depicts an example data network platform, according to an embodiment of the present invention.

FIG. 6 depicts an example data network platform 60, according to an embodiment of the present invention. In an example embodiment of the present invention, a monitoring computer 61 is coupled communicatively to the SCADA system 555 and/or the data network 550. An example embodiment of the present invention may be implemented in which the monitoring computer 61 is coupled communicatively to the SCADA system 555 over the data network 550.

The data network 550 may comprise a packet switched network operable for communicating data using a transport control protocol and/or a networking protocol (e.g., 'TCP/IP'). The data network 550 may comprise, at least in part, a telephone network, one or more wide area networks (WANs), local area networks (LANs), secured networks and sub-networks (subnets), a network related to the SCADA system 555, and/or one or more public and/or private internetworks, database networks, network area storage (NAS) systems), storage area networks (SANs), including (but not limited to) the public internet.

The monitoring computer 61 is operable for receiving, via SCADA system 555 and/or data network 550, the data signals from the at least one monitor/instrument 524, and for processing one or more computations therewith. The monitoring computer 61 may be operable, further, for updating and/or querying at least one database 62 in relation to the processed computations. The monitoring computer 61 and the database 62 may be coupled directly, via a LAN, over the network 550, and/or via the SCADA system 555. The database 62 may comprise stored data comprising historical, trend, design, operational, emergency, maintenance, and other information related to the data signals received from the at least one monitor instrument 524.

Based on the processed computations and/or upon the querying of the database 62, the monitoring computer may be operable, further, for taking one or more actions. For example, upon the processed computations indicating that a characteristic property of the fluid 36 fails to meet an associated threshold value, exceeds an associated set point value, and/or deviates from an allowable band or range, the monitoring computer 61 may, automatically, log an event corresponding to the indication, update the database 62 in relation to the indication and/or the logged event, transmit a notification to an operator, supervisor and/or computer, control console, annunciator, and/or automated control system and maintenance tasking planner and scheduler, and/or annunciate a corresponding indication, warning, or alarm.

With reference again to FIG. 5, the at least one instrument (e.g., 524) of the system 500 may comprise a moisture content hysteresis monitor 523. The moisture content hysteresis monitor 523 comprises a first instrument 521, and at least a second instrument 522.

The first instrument 521 is in contact (and/or immersed, at least partially) with the fluid 36 of the convective flow current 536, within the first tubular assembly 100 of the pair and upstream of the upper header 471. The second instrument 522 is in contact (and/or immersed, at least partially) with the fluid 36 of the convective flow current 536, within the second tubular assembly 100 of the pair and downstream of the lower header 472.

The sensor/probe 597 associated with the instrument 521 and/or the instrument 522 is/are operable for sensing and/or analyzing, and correspondingly generating data signals, relating to one or more characteristic properties of the fluid 36, as described above in relation to the sensor/probe 597 (e.g., associated with the at least one monitor/instrument 524). An example embodiment may be implemented in which the sensed characteristic relates to a temperature, pressure and/or a moisture content of the fluid 36. A differential pressure between the portion (or volume) of the fluid contained within the upper header 471 and the portion or volume of the fluid contained within the lower header 472 may also thus be sensed.

The sensor/probes 597 associated with the instrument 521 and/or the instrument 522 may also be operable for sampling a portion of the fluid 36, and transporting the sampled fluid portion to the instruments 521 and/or 522, which may be operable, further, for the sensing and/or analyzing, and corresponding generating data of the signals, relating to one or more characteristic properties of the fluid 36 (e.g., as described above in relation to the at least one monitor/instrument 524).

In an example embodiment of the present invention, the data signals related to the sensed characteristic properties of the fluid 36, generated by the instrument 521 and the instrument 522, and/or by the sensors 597 associated each therewith, are communicated to the moisture content hysteresis monitor 523. The moisture content hysteresis monitor 523 is operable for measuring a moisture content and a temperature of the fluid 36, within the convective flow current 536, at the instrument 521 (e.g., upstream therein, relative to the upper header 471) and at the instrument 522 (e.g., downstream of the lower header 472).

The moisture content hysteresis monitor 523 may be operable, further, for computing a hysteresis related to the measured moisture content, and/or communicating data signals corresponding thereto, over the data network 550 and/or the SCADA system 555. The computed hysteresis relates to monitoring of a dynamic movement of the moisture between the fluid 36 and paper and/or other cellulose containing solid dielectric material within the transformer 400. The movement of the moisture, between the paper insulation and the fluid 36 may relate to the loading of the transformer 400 over time.

An example embodiment of the present invention may be implemented in which the monitoring of the moisture content and the temperature of the fluid 36, and/or the computation of the moisture related hysteresis is performed as described in the Roizman reference (Int'l Pat. Appl. Pub. No. WO/2015/067844). A differential pressure (e.g., between the portion or volume of the fluid contained within upper header 471 and the portion or volume of the fluid contained within lower header 472) may also be monitored.

One of the probes 597 may be associated with a sample flask 588. Upon insertion through one of the ball valves 599, the sample flask 588 may be vented (e.g., by opening a valve on a distal end thereof, relative to the ball valve) and filled under a hydraulic pressure differential between the fluid 36 within the convective flow current 536 and the atmosphere 499 to which the flask 588 is vented (e.g., by opening a fill valve on a proximate end, relative to the ball valve 599 and the sensor 597). Upon filling the sample flask 588 (e.g., and observing a small amount of the fluid 36 emerge therefrom through its vent valve), the sample flask may be sealed (e.g., by closing the vent valve and the fill valve). The probe 597 associated with the sample flask 588 may then be removed from the ball valve 599, and the system sealed by closing the ball valve. The sample flask 588 may then be transported for analysis elsewhere (e.g., at a laboratory remote, at least to some degree, from the transformer 400).

An example embodiment of the present invention may be implemented in which the analysis performed in the sensor/probes 597, the at least one monitor instrument 524, the instruments 521 and 522, the moisture content hysteresis monitor 523, the data signals generated in relation thereto, and/or the laboratory analysis relate to the characteristic physical and/or chemical properties of the fluid 36. The properties and characteristics of the fluid 36 may include, but are not limited to, temperature, moisture content, moisture content related hysteresis, dielectric strength, insulation power factor, DGA, IFT, viscosity, density, specific gravity, spectroscopy (e.g., mass, NMR, Ramen, IR and other optical frequency bands), spectrophotometry, color, turbidity turgidity, carbonization, pressure and/or differential pressure (e.g., between an upper header and a lower header), and/or suspended solids, suspended metallic particles, dissolved and/or ionized metals, and the presence of metal ligands and/or other chelated materials. The metals may comprise copper, silver, and metals with which others may be alloyed and/or amalgamated.

An example embodiment of the present invention may be implemented in which the sensor/probes 597, the at least one monitor instrument 524, the instruments 521 and 522, the moisture content hysteresis monitor 523, the monitor computer 61, and/or a computer associated with each of the database 62, the SCADA system 555, and/or the network 550 comprises a computer platform.

Example Computer Platform.

FIG. 7 depicts an example computer platform 700, according to an embodiment of the present invention. An example embodiment may be implemented in which one or more components of the computer platform 700 are configured in electronic devices or computer based hardware, software stored physically, electronically, electromagnetically, optically, etc. in non-transitory computer readable storage media such as dynamic memory, flash memory, drives, caches, buffers, registers, latches, memory cells, or the like.

The computer platform 700 may comprise one or more components of the at least one monitor instrument 524. The monitor instrument 524 may comprise a fluidics module 776, which is operable for providing access to the sampled portion of the fluid 36 to an analysis module 777. The analysis module 777 is operable for performing one or more of the analytic and/or diagnostic tests on the sample portion of the fluid 36.

The fluidics module 776 may be operable, further and upon the performance of the analytic/diagnostic testing, for returning the sampled portion to the convective flow current 536. A data signal generator 772 is operable for generating the data signals based on an outcome of the analytic/diagnostic tests. A controller module 775 may be operable for controlling an operation of the fluidics module 776, the analysis module 777, and/or the data signal generator 772.

The computer platform 700 may also comprise a touchscreen display 725. An example embodiment may be implemented in which a graphical user interface (GUI) 780 is rendered and actuated by the touchscreen display 725.

The computer platform 700 may comprise an interface 718 and one or more network links 720 operable therewith. The computer platform 700 may communicatively couple with the SCADA system 555 and/or the data network 550 via the interface 718 and the one or more network links 720. The computer platform 700 may be operable for exchanging data with a remote computer 798 (e.g., the monitor computer 61, database 62, represented therewith).

The computer platform 700 may be operable for exchanging data with the network 550 based on packet-switching according to transfer control and internetworking protocols (e.g., TCP/IP).

The computer platform 700 comprises a plurality of electronic components, each of which is coupled to a data bus 702. The data bus 702 is operable for allowing each of the multiple, various electronic components of computer platform 700 to exchange data signals with each of the other electronic components.

The electronic components of the computer platform 700 may comprise integrated circuit (IC) devices, including one or more microprocessors. The electronic components of the computer platform 700 may also comprise other IC devices, such as a microcontroller, field-programmable gate array (FPGA) or other programmable logic device (PLD) or application-specific IC (ASIC).

The microprocessors may comprise a central processing unit (CPU) 704. The CPU 704 is operable for performing general data processing functions related to operations of the GUI and other components of the computer platform 700. The electronic components of the computer platform 700 may also comprise one or more other processors 744.

For example, the other microprocessors may comprise a graphics processing unit (GPU) and/or digital signal processor (DSP) 704, which are each operable for performing data processing functions that may be somewhat more specialized than the general processing functions, as well as sometimes sharing some processing functions with the CPU 704.

One of the processors 744 may also be operable as a "math" (mathematics) coprocessor. The math co-processor, DSP and/or GPU ("DSP/GPU") 744 are operable for performing computationally intense data processing. The computationally intense processing may relate to the analysis and/or diagnostic testing performed by the at least one monitor instrument 524 upon the fluid 36. One of the microprocessors may comprise a monitor 733 associated with the at least one monitor instrument 524, and/or dedicated and/or specialized in processing the analytic/diagnostic data signals generated therewith.

The data processing operations comprise computations performed electronically by the monitor 733, CPU 704, and the DSP/GPU 744. The microprocessors may comprise components operable as an ALU, a FPU, and associated memory cells. The memory cells comprise non-transitory data storage media, which may be configured as caches (e.g., "L1," "L2"), registers, latches and/or buffers.

The memory cells are operable for storing data electronically in relation to various functions of the processor. A translational look-aside buffer (TLB) may be operable for optimizing efficiency of use of content-addressable memory (CAM) by the CPU 704, and/or the DSP/GPU 744, etc.

The computer platform 700 also comprises non-transitory computer readable storage media operable for storing data, e.g., electronically. For example, the computer readable storage media comprises a main memory 706, such as a random access memory (RAM) or other dynamic storage medium. The main memory 706 is coupled to data bus 702 for storing information and instructions, which are to be executed by the CPU 704, etc.

The main memory 706 may also be used for storing temporary variables or other intermediate information during execution of instructions by the CPU 704, etc. Other memories (represented in the present description with reference to the RAM 706) may be installed for similar uses by the DSP/GPU 744, and/or the monitor processor 733.

The computer platform 700 may comprise, further, a read-only memory (ROM) 708 or other static storage medium coupled to the data bus 702. The ROM 708 is operable for storing static information and instructions for use by the CPU 704. In addition to the RAM 706 and the ROM 708, the non-transitory storage media may comprise at least one data storage device 710. The data storage device 710 is operable for storing information and instructions and allowing access thereto.

The data storage device 710 may comprise a magnetic disk drive, flash drive, or optical disk drive (or other non-transitory computer readable storage medium). The data storage device 710 comprises non-transitory media coupled to data bus 702, and may be operable for providing a "virtual memory" function. The virtual memory operations of the storage device 710 may supplement, at least temporarily, storage capacity of other non-transitory media, such as the RAM 706.

The non-transitory storage media comprises instructions 783, which are stored (e.g., electronically, magnetically, optically, physically, etc.) in relation to software for programming, controlling, and/or configuring operations of the computer platform 700 and its components, including the at least one monitor instrument 524, etc. The instructions 783 may also relate to the performance of one or more steps of an analysis/diagnostic process, such as the example method 80 for monitoring a fluid (FIG. 8A), and/or the example method 800 (FIG.8B) for monitoring a power device (e.g., in which the fluid is disposed).

Instructions, programming, software, settings, values, and configurations, etc. related to the method 80, the operation of the at least one monitor instrument 524 and its components, and other operations of the computer platform 700 are stored (e.g., magnetically, electronically, optically, physically, etc.) by the storage medium 710, memory, etc.

The computer platform 700 comprises a user-interactive display configured as the touchscreen 725, which is operable as a combined display and GUI 780. The touchscreen 725 may comprise a liquid crystal display (LCD), which is operable for rendering images by modulating variable polarization states of an array of liquid crystal transistor components. The touchscreen 725 also comprises an interface operable for receiving haptic inputs from a user.

The haptic interface of the GUI 780 and touchscreen 725 may comprise, e.g., at least two arrays of microscopic (or transparent) conductors, each of which is insulated electrically from the other and disposed beneath a surface of the display 725 in a perpendicular orientation relative to the other. The haptic inputs comprise pressure applied to the surface of the touchscreen 725 and GUI 780, which cause corresponding local changes in electrical capacitance values proximate to the pressure application that are sensed by the conductor grids to effectuate a signal corresponding to the input. Images and video data may also be presented on the display 725.

The touchscreen 725 may be implemented operably for rendering images over a heightened (e.g., high) dynamic range (HDR). The rendering of the images may also be based on modulating a back-light unit (BLU). For example, the BLU may comprise an array of light emitting diodes (LEDs). The LCDs may be modulated according to a first signal and the LEDs of the BLU may be modulated according to a second signal. The touchscreen 725 may render an HDR image by coordinating the second modulation signal in real time, relative to the first modulation signal.

Other display technologies may also (or alternatively) be used. For example, the display 725 may comprise an organic LED (OLED) array. The display 725 may also (or alternatively) comprise a display operable over a standard dynamic range (SDR), sometimes also referred to as a "low dynamic range" (LDR).

An input receiver 714 may comprise one or more electromechanical switches, which may be implemented as buttons, escutcheons, microelectromechanical sensors (MEMS) or other sensors, dual in-line package (DIP) switch, etc. The input receiver 714 may also comprise cursor and trigger controls such as a mouse, joystick, etc. and/or a keyboard. The keyboard may comprise an array of alphanumeric and/or ideographic, syllabary based keys operable for typing corresponding letters, number, and/or other symbols. The keyboard may also comprise an array of directional (e.g., "up/down," "left/right") keys, operable for communicating commands and data selections to the CPU 704 and for controlling movement of a cursor rendering over the touchscreen display 725. The input receiver 714 may allow inputs for controlling the performance of the fluid monitoring process 80.

The directional keys may be operable for presenting two degrees of freedom of a cursor, over at least two perpendicularly disposed axes presented on the display component of the touchscreen 725. A first 'x' axis is disposed horizontally. A second 'y' axis, complimentary to the first axis, is disposed vertically.

Execution of instruction sequences contained in the storage media 710 and main memory 706 cause the CPU 704 to perform processing related to general operations of the computer platform 700, the DSP/GPU 744 to perform various other processing operations, and the components of the at least one monitor instrument to perform processing steps related to the example method 80. Additionally or alternatively, hard-wired circuitry may be used in place of, or in combination with the software instructions. Thus, the computer platform 700 is not limited to any specific combination of circuitry, hardware, firmware, or software.

The term "computer readable storage medium," as used herein, may refer to any non-transitory storage medium that participates in providing instructions to the various processor components of the computer platform 700 for execution. Such a medium may take various forms including, but not limited to, non-volatile media, volatile media, and transmission media. Non-volatile media comprises, for example, configured/programmed active elements of the GUI 780 and components of the at least one monitor instrument 524, the CPU 704, the DSP/GPU 744, the non-transitory image related media 710, stored instructions 783, and other optical, electronic, or magnetic media. Volatile media comprises dynamic memory associated, e.g., with the RAM 706.

Transmission media comprises coaxial cables, copper wire and other electrical conductors and fiber optics, including the wires (and/or other conductors or optics) that comprise the data bus 702.

Transmission media can also take the form of electromagnetic radiation (e.g., light waves), such as may be generated at a radio frequency (RF), and infrared (IR) and other optical frequencies. Data communications may also be effectuated using other means, including acoustic (e.g., sound related) or other mechanical, vibrational, or phonon related media.

Non-transitory computer-readable storage media may comprise, for example, flash drives such as may be accessible via universal serial bus (USB) or any medium from which the computer platform 700 can access, read, receive, and retrieve data.

Various forms of non-transitory computer readable storage media may be involved in carrying one or more sequences of one or more instructions to CPU 704 for execution. For example, the instructions may initially be carried on a magnetic or other disk of a remote computer (e.g., computer 798). The remote computer can load the instructions into its dynamic memory and send the instructions over networks 550.

The printing system 100 can receive the data over the network 550 and use an infrared (IR), radio frequency (RF), or other transmitter means to convert the data to corresponding signals. An IR, RF or other signal detector or receiver ("receiver") coupled to the data bus 702 can receive the data carried in the corresponding signals and place the data on data bus 702. The operations associated with the transmitter and the receiver may be combined in a transmitter/receiver (transceiver) means. The transmitter, receiver and/or transceiver means may be associated with the interfaces 718.

The data bus 702 carries the data to main memory 706, from which CPU 704 and the DSP/GPU 744 retrieve and execute the instructions. The instructions received by main memory 706 may optionally be stored on storage device 710 either before or after execution by CPU 704.

The interfaces 718 may comprise a communication interface coupled to the data bus 702. The communication interface is operable for providing a two-way (or more) data communication coupling to a network link 720, which may connect wirelessly over RF to the network 550. Wireless communication may also be implemented optically, e.g., at IR frequencies.

Signals may be exchanged via the interfaces 718 with an external device 798 (e.g., another computer or external storage device) through a compatible communication port, such as one or more network links 720. The input receiver 714 may provide signals to the GUI 41 and other components of the monitor instrument 524 and the computer platform 700 via the network links 720.

In any implementation, the communication interface 718 sends and receives electrical, electromagnetic or optical signals that carry digital data streams representing various types of information. The network link 720 provides data communication through the network 550 to other data devices. The input receiver 714 may provide signals to the at least one monitor instrument 524 and other components of the computer platform 700 via the network links 720 and/or the data communications network 550.

The network 550 may use one or more of electrical, electromagnetic, and/or optical signals carrying digital data streams. The signals sent over the network 550 and through the network link 720 and communication interface 718 carry the digital data to and from the at least one monitor instrument 524. The monitor instrument 524 can send messages and receive data, including program code, through the network 550 and/or SCADA system 555, network link 720 and communication interface 718.

At least one component of the computer platform 700 (e.g., the at least one monitor instrument 524) may be operable for performing one or more analytic/diagnostic testing functions on the sampled portion of the fluid 36, generating corresponding data signals based on results of the tests and the characteristic physical and/or chemical properties of the fluid 36, and communicating the generated data signals over the network 550 and/or the SCADA system 555. The computer platform 700 may thus be operable for performing one or more processes related to the monitoring of the fluid 36 and/or the monitoring of the power device.

One or more components of the computer platform 700 may be operable in relation to monitoring a transformer or other power device and/or the fluid within the power device, which insulates components of the power device electrically and transfers heat generated therewith to a heat sink. For example, the CPU 704, GPU/DSP 744, RAM 706, storage 710, and/or the instructions 783 stored therewith (and/or with other non-transitory storage media), and/or the monitor instrument 524 may be operable in relation to the monitoring of the fluid and/or the monitoring of the power device. In an example embodiment, the operations and the instructions may relate to performing the process 80 (FIG. 8A) and/or the process 800 (FIG.86).

Example Processes.

Figure 8A:
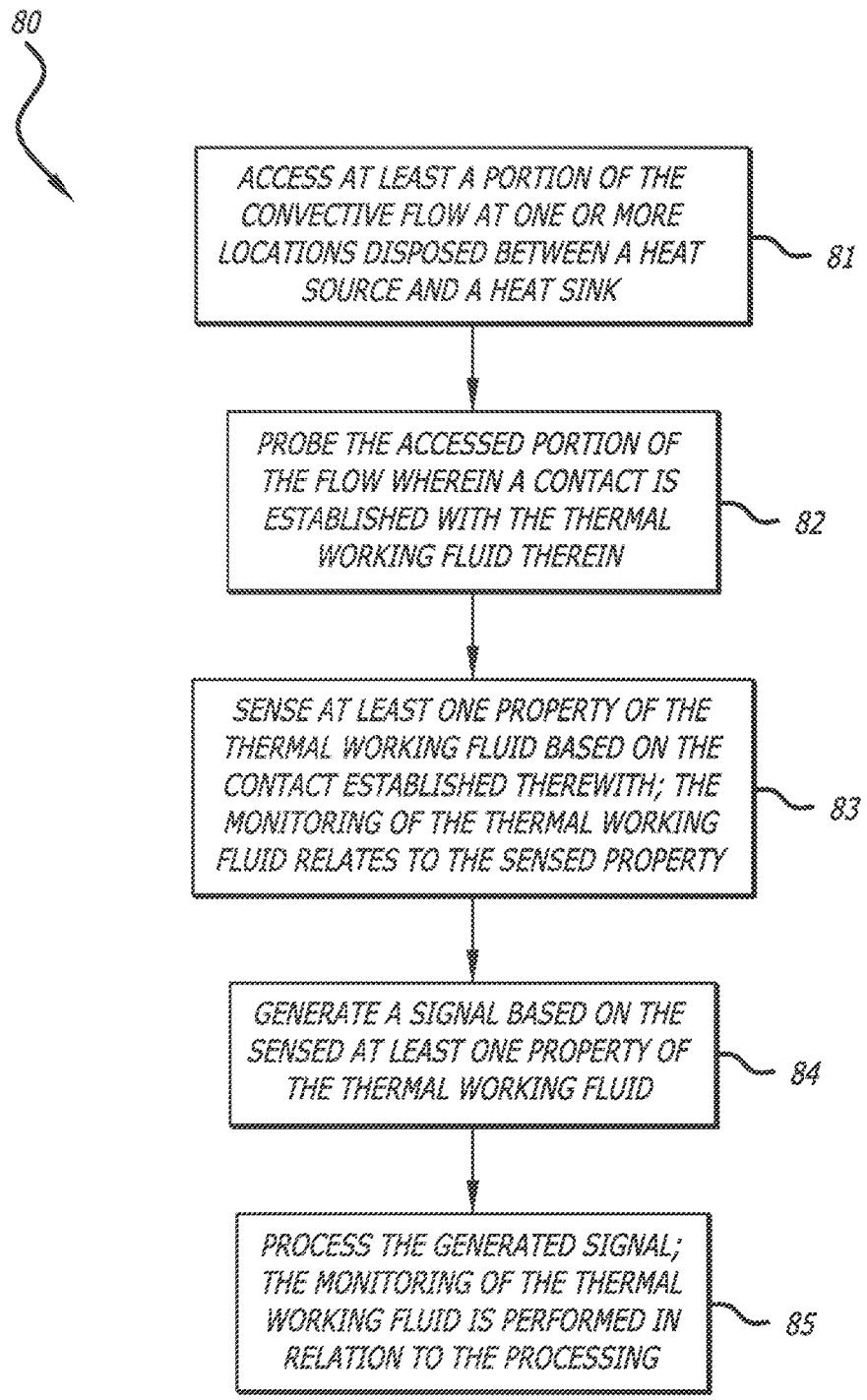
FIG. 8A depicts a flowchart for an example fluid monitoring process, according to an embodiment of the present invention.

FIG. 8A depicts a flowchart for an example method 80 for monitoring a fluid, according to an embodiment of the present invention. The fluid may comprise a thermal working fluid circulating in a convective flow.

In step 81, at least a portion of the convective flow is accessed at one or more locations disposed between a heat source and a heat sink.

In step 82, the accessed at least portion of the flow is probed, in which a contact is established with the thermal working fluid therein.

In step 83, at least one property of the thermal working fluid is sensed, based on the contact established therewith. The monitoring a thermal working fluid relates to the sensed at least one property thereof.

The method 80 may also comprise step 84, in which a signal is generated based on the sensed at least one property of the thermal working fluid.

The method 80 may also comprise step 85, in which the generated signal is processed. The processing of the generated signal may relate to monitoring the power device, e.g., in which the thermal working fluid is disposed.

Figure 8B:
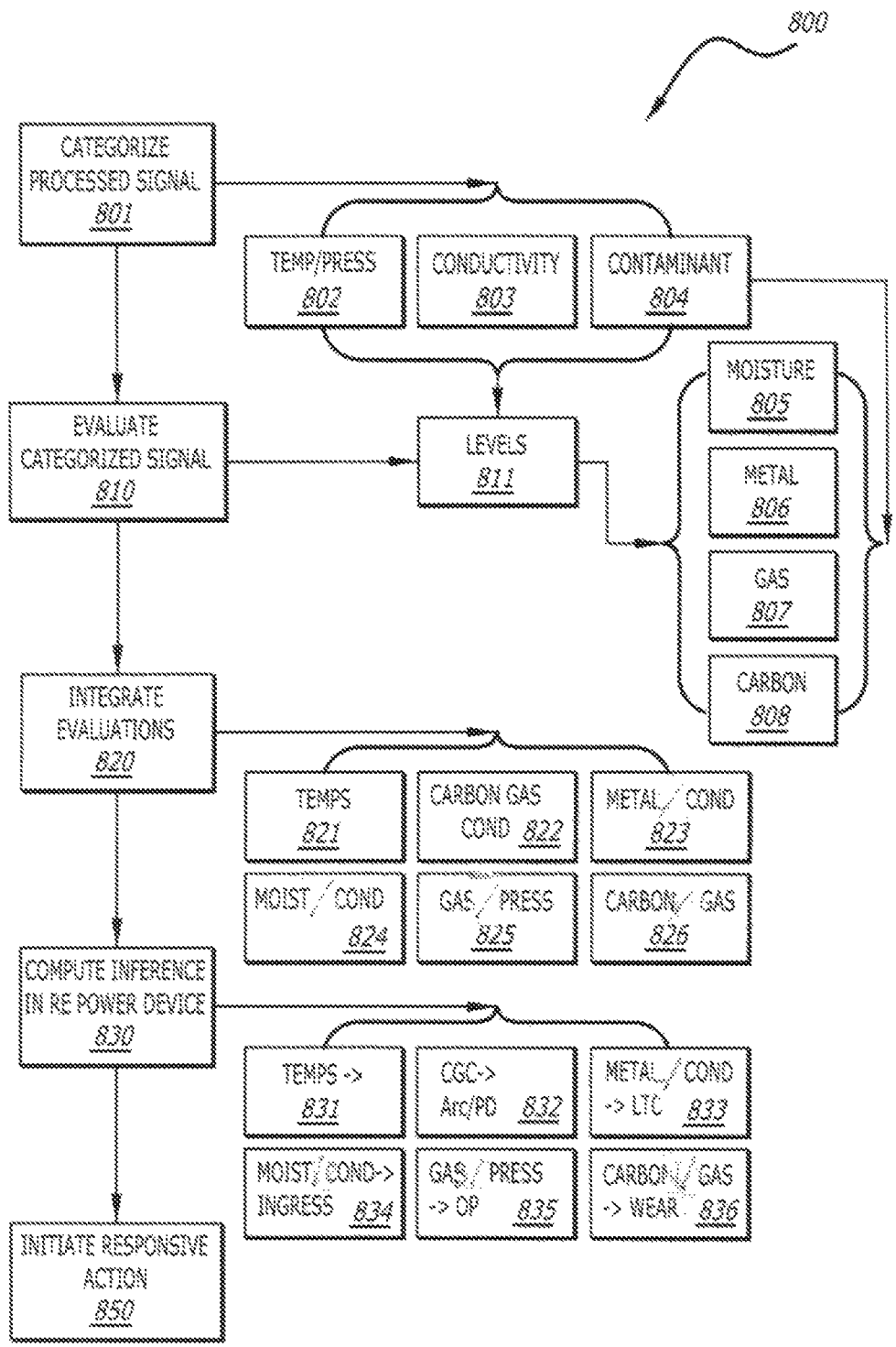
FIG. 8B depicts a flowchart for an example process for monitoring a power device, according to an embodiment of the present invention.

FIG. 8B depicts a flowchart for an example process 800 for monitoring a power device, according to an embodiment of the present invention. The process 800 may relate, at least in part, to one or more steps of the process 80 (FIG. 8A). For example, one or more steps of the process 800 may relate to the performance of the processing of the generated signal, e.g., step 85 of the process 80.

In step 801, the signal processed in step 85 of the process 80 (FIG. 8A) is categorized with respect to a particular property of the fluid to which it relates. For example, the processed signal may be characterized as pertaining to a physical characteristic of the fluid, such as temperature and/or pressure, as represented with the temperature/pressure (Temp/Press) category 802. The processed signal may comprise a conductivity category 803, which may pertain to properties such as dielectric strength, resistivity, conductance, and/or insulation power factor. The processed signal may be characterized as pertaining to a chemical characteristic of the fluid, such as a material identity and quality, as represented with the contaminant category 804.

The categories may comprise a plurality of subcategories. For example, the contaminant category 804 may comprise a moisture category 805, a metal category 806, a gas category 807, and a carbon category 808. The moisture category 805 relates to the presence of moisture in the fluid. The metal category 806 relates to the presence of metal particles, ions, ligands, etc. in the fluid. The gas category 807 relates to the presence of dissolved gas (or materials related to the presence thereof) in the fluid. The gas category 807 may comprise a plurality of subcategories, each relating to a different gas entity, such as oxygen, hydrogen, hydrocarbons, combustion products, etc. The carbon category 808 relates to the presence of carbonization in the fluid. Categories may also be included, which relate to other materials, contaminants, etc.

In step 810, each of the categorized signals are evaluated in relation to a level, magnitude, concentration, degree, and/or quantity ("level") 811. A level may thus be computed in relation to each of the temperature/pressure level 802, the conductivity level 803, and/or the contaminant level 804. A level may also be computed in relation to each of the subcategories, including the moisture category 805, the metal category 806, the gas category 807, the carbon category 808, and/or any other category or subcategory.

In step 820, the evaluated signals corresponding to each of two or more of the categories and subcategories are integrated. For example, the categorized temperature levels evaluated in relation to the processed outputs of the temperature sensors at two or more of the headers may be integrated.

In step 830, an inference may be computed in relation to an operating condition of the transformer or other power device. For example, the temperature levels 802 evaluated, e.g., in relation to each of the temperature sensors at the two or more headers may be integrated in relation to computing the volume of the fluid in the power device. An example embodiment may be implemented in which an inference 831 may be computed the computation of the fluid volume is computed based on the integrated temperature levels 821, e.g., at least in part using techniques as described in the Watson reference.

The evaluated levels 811 corresponding to the carbon category 808, the gas category 807, and/or the conductivity category 803 may comprise an integration 822. An example embodiment may be implemented in which an inference 832 is computed in relation to an occurrence of arcing and/or partial discharge within the power device.

The evaluated levels 811 corresponding to the metal category 806 and/or the conductivity category 803 may be integrated. An example embodiment may be implemented in which an inference 823 is computed in relation to an operating condition, maintenance or repair condition, electrical, electromechanical, or mechanical wear or damage to a load tap changer (LTC) component of the power device, or the occurrence of an electrical fault within with the device. An inference 824 may also be computed in relation to a detected and/or measured moisture level and/or conductivity level of the fluid. Elevated moisture and/or conductivity levels may indicate one or more of an ingress of water or airborne moisture from ambient outside atmosphere into the transformer tank, condensation "dripping" into the fluid from an inner surface thereof, or absorbance of the moisture, such as via hygroscopy of moisture that may be present in the gas blanket, or from other sources. The elevated conductivity levels may also indicate a condition related to electrical components of the transformer, such as the LTC, coils and core, and/or and other metallic components such as the transformer tank.

The evaluated levels 811 corresponding to the pressure/temperature category 802, the moisture category 805, the gas category 807, and/or the conductivity category 803 may be integrated. An example embodiment may be implemented in which an inference 834 is computed in relation to an indication of the ingress of moisture into the power device.

The evaluated levels 811 corresponding to the moisture category 805, the gas category 807, and/or the pressure/temperature category may be integrated. Integrating the evaluated levels 811 of the temperature/pressure category 802, and the moisture category 805, an example embodiment may be implemented in which the inference 834 may be computed in relation to an indication of moisture hysteresis within the power device, e.g., at least in part using techniques as described in the Roizman reference, based on an integration of the moisture.

The evaluated levels 811 corresponding to the gas category 807, and/or the pressure/temperature category 802 may comprise an integration 825. An example embodiment may be implemented in which the inference 835 may be computed in relation to an overpressure or underpressure condition within the electrical device.

The evaluated levels 811 corresponding to the carbon category 808, the gas category 807, the pressure/temperature category 802, and/or the conductivity category 803 may comprise an integration 826. An example embodiment may be implemented in which the inference 836 of an occurrence of wear, aging, oxidation, and/or arcing and/or partial discharge within the electrical device and the fluid.

In step 850, an action is initiated based on one or more of the computed inferences. For example, an alarm may be triggered, a warning may be annunciated, or an indication presented if one of the evaluated levels 811 reaches or surpasses a high level or low level threshold. For a situation in which the integrated evaluation 820 or the computed inference 830 indicates a suboptimal operating condition of the power device, a maintenance action may be indicated and planned. For a situation in which the integrated evaluation 820 or the computed inference 830 indicates a dangerous operating condition of the power device, an emergency operation may be initiated. For example, a load dispatch entity may be informed, e.g., with an alarm. Load shedding may be commenced, e.g., automatically. The transfer of electrical loads from the affected device to an alternate source may also be commenced.

An example embodiment of the present invention thus relates to a method for monitoring an electrical power device. The method comprises sensing a property of a fluid of the power device with one or more instruments. The one or more instruments each comprise a probe placed, removably, into contact with the fluid through a valve, with the valve disposed in an open position and mounted in a penetration within a lateral envelope of a pipe. The pipe is disposed in a header, through which a flow of the fluid is coupled, longitudinally, between a tank of the power device and a cooling device. A signal is generated, based on the sensed property with the one or more instruments. Data related to the generated signal is exchanged with a network coupled communicatively with the one or more instruments. The exchanged data is processed in relation to the monitoring of the power device.

The heat source may comprise a power transformer. The heat sink may comprise an ambient atmosphere surrounding a radiator through which the thermal working fluid flows. Alternatively (or additionally), the heat sink may comprise a coolant fluid. The thermal working fluid flows through a first section of a heat exchanger. The coolant fluid flows through a second section of the heat exchanger isolated, hydraulically, from the first section. A heat loading on the working fluid is transferred to the coolant fluid through the heat exchanger, or the radiator.

In an example embodiment of the present invention, a valve is installed laterally, relative to the convective flow, at the one or more locations disposed between the heat source and the heat sink. The accessing of the at least a portion of the convective flow of the thermal working fluid may thus comprise opening the valve.

The probing the accessed at least portion of the flow may comprise immersing a probe, at least partially, within the at least portion of the thermal working fluid through the opened valve. The contact may thus be established with the thermal working fluid based on the at least partial immersion therein.

An example embodiment of the present invention relates to a system for sensing at least one property of a fluid circulating in a flow between a power device, such as a transformer or reactor, and an associated cooling device, such as a radiator or a heat exchanger. The system comprises at least one assembly, comprising a tubular section installed, and coupling the flow of the fluid, longitudinally between a tank of the power transformer and the cooling device. The tubular section is penetrated with one or more access penetrations disposed laterally in relation to the flow of the fluid. The system also comprises at least one instrument, comprising a probe and operable for sensing the at least one property of the fluid. The system comprises, further, a valve disposed within the one or more access penetrations and comprising a closed position, and an open position. In the open position, the probe of the at least one instrument is placed in a contact with the flow of the fluid through the valve.

An example embodiment of the present invention relates to a power transformer device. The power transformer comprises an electrically active section immersed within a dielectric working fluid disposed within a tank. The electrically active section of the transformer comprises at least two conductive windings, each of the windings operable for conducting an electrical current, and coiled about a magnetically permeable core immersed within the dielectric fluid. The core is operable for inducing a first electrical voltage in a first of the at least two windings based on a second electrical voltage associated with at least a second of the at least two windings.

The power transformer also comprises a cooling section coupled mechanically to the tank at a first penetration disposed proximate to an upper portion of the tank, and a second penetration disposed proximate to a lower portion of the tank, relative to the upper portion. The cooling section may comprise a radiator and/or a heat exchanger, and is operable for cooling the electrically active section. During an operation of the power transformer, a heat loading produced in the electrically active section is transferred to the dielectric working fluid, which flows convectively about the windings and the core immersed therein. The dielectric working fluid, thus heated, flows from the first penetration in a convectively driven flow to the cooling section. Through the cooling section, the heat loading is transferred from the thermal working fluid to a heat sink. The flow of the thermal working fluid, thus cooled, returns to the tank through the second penetration.

The power transformer comprises, further, at least one "transport" component operable for transporting at least a portion of the convectively driven flow of the dielectric working fluid between the tank and the cooling section. The at least one transport component comprises a tubular section installed, and coupling the at least portion of the flow of the fluid, longitudinally between the tank and the cooling section. The tubular section is penetrated, laterally in relation to the transported flow of the fluid, with one or more access penetrations. The at least one transport component also comprises a valve, disposed within the one or more access penetrations. The valve may comprise a ball valve and comprises a closed position, and an open position. In the open position, the flow of the at least portion of the fluid is accessible by a probe of an instrument, which is placed in a contact with the flow of the fluid through the valve.

An example embodiment of the present invention relates to a method for monitoring a thermal working fluid circulating in a convective flow. The method comprises accessing at least a portion of the convective flow at one or more locations disposed between a heat source and a heat sink. For example, the heat source may comprise a tank of a power transformer, in which electrically active components are immersed within the thermal working fluid. The method also comprises probing the accessed at least portion of the flow, to establish a contact with the thermal working fluid therein. At least one property of the thermal working fluid is sensed based on the contact established therewith. The monitoring of the thermal working fluid relates to the sensing of the at least one property.

An example embodiment of the present invention relates to an apparatus for coupling a flow of a thermal working fluid between a heat source and a heat sink. The heat source may comprise, for example, a power transformer. The heat sink may comprise an ambient atmosphere surrounding a radiator apparatus, through which the thermal working fluid flows. Alternatively (or additionally), the heat sink may comprise a coolant fluid, which flows through a heat exchanger apparatus. The thermal working fluid may flow through a first section of a heat exchanger. The coolant fluid flows through a second section of the heat exchanger isolated, hydraulically, from the first section. A heat loading on the working fluid is transferred to the coolant fluid through the heat exchanger.

The apparatus comprises a substantially tubular section disposed between the heat source and the heat sink and longitudinally, relative to the flow of the thermal working fluid. For example, the tubular section may be disposed between a tank of the transformer and the radiator or heat exchanger. One or more access penetrations through a wall of the substantially tubular section are disposed laterally in relation to the flow of the fluid. A valve is disposed within the one or more access penetrations and comprising a closed position, and an open position. In the open position, a probe operable for sensing at least one property of the thermal working fluid is immersible, at least partially, in the flow of the fluid through the valve.

An example embodiment of the present invention relates to a system for monitoring one or more power transformers. The system comprises a data network and/or a SCADA system, and a computer coupled communicatively to the data network or SCADA system. The computer is operable in relation to the monitoring of the one or more power transformers. The system also comprises at least one instrument comprising a probe. The at least one instrument is operable for sensing a property of a thermal working fluid circulating in a flow between a tank of each of the one or more transformers and a cooling device associated therewith. The probe of the at least one instrument is placed in a contact with at least a portion of the flow of the fluid at a location between the tank and the associated cooling device. The at least one instrument is operable, further, for generating a data signal, and for sending the data signal, over the data network or the SCADA system, to the computer. The monitoring of the one or more transformers is performed in relation to the data signal sent to the computer.

Example embodiments of the present invention are thus described in relation to an apparatus for sensing properties of a fluid. The fluid may comprise an insulating fluid and coolant for an electrical power device, such as a transformer or reactor. The apparatus comprises a pipe section, a valve such as a ball valve, and at least one instrument. The pipe section comprises an envelope, through which a flow of the fluid is coupled between a tank of the electrical power device and a cooling device, such as a radiator or other heat exchanger. The envelope is disposed about a longitudinal axis, and comprises one or more penetrations disposed laterally in relation to the longitudinal axis. The valve is disposed within the one or more penetrations and has a closed position and an open position. The instrument is operable for the sensing of the fluid properties, and has a probe disposed in contact with the fluid through the valve in the open position. The instrument may be disposed removably through the valve. The instrument may be disposed, interchangeably, with the probe of at least a second instrument. Example embodiments relate to a system, an instrument, and a method for sensing the fluid properties.

An example embodiment of the present invention relates to a method for monitoring a power device. The method comprises processing signals from each of the sensors. The method may also comprise categorizing the processed signals, and evaluating the categorized signals. The evaluations of multiple categorized signals may be integrated, and an inference computed in relation to an operating condition of the power device. A responsive action may be implemented automatically based on the computed inferences. Embodiments of the present invention thus relate to the promotion of reliable transformer operations. Example embodiments of the present invention also relate to sampling the transformer insulating fluids and to testing properties of the sampled fluids that may characterize its ongoing usefulness, and thus promoting associated reliability of the transformer operations. An example embodiment of the present invention relates, further, to monitoring the properties of the transformer insulating fluids over time, with continuous and/or on-demand availability, and without interrupting the operations of the transformer, or disrupting the real time supply, flow, or utility of the fluids during the transformer operations.

For clarity and brevity, as well as to avoid unnecessary or unhelpful obfuscating, obscuring, obstructing, or occluding features of an example embodiment, certain intricacies and details, which are known generally to artisans of ordinary skill in related technologies, may have been omitted or discussed in less than exhaustive detail. Any such omissions or discussions are neither necessary for describing example embodiments of the invention, nor particularly relevant to understanding of significant elements, features, functions, and aspects of the example embodiments described herein.

In the specification and/or figures, typical embodiments of the invention have been disclosed. The present invention is not limited to such example embodiments. The use of the term "and/or" includes any and all combinations of one or more of the associated listed items, and the term "or" is used in an inclusive (and not exclusive) sense. The figures are schematic representations and so are not necessarily drawn to scale. Unless otherwise noted, specific terms have been used in a generic and descriptive sense and not for purposes of limitation.

In an example embodiment of the present invention, an apparatus monitors a fluid. The fluid monitoring apparatus comprises a pipe section, a valve such as a ball valve, and at least one instrument. The pipe section comprises an envelope, through which a flow of the fluid is coupled between a tank of an electrical power device, such as a transformer or reactor, and a cooling device, such as a radiator or other heat exchanger. The envelope is disposed about a longitudinal axis, and comprises one or more penetrations disposed laterally in relation to the longitudinal axis. The valve is disposed within the one or more penetrations and has a closed position and an open position. The instrument is operable for the sensing of the fluid properties, and has a probe disposed in contact with the fluid through the valve in the open position. The instrument may be disposed removably through the valve. The instrument may be disposed, interchangeably, with the probe of at least a second instrument. Example embodiments relate to a system, an instrument, and a method for sensing the fluid properties.

What is claimed is:

1. An apparatus configured for sensing one or more properties of a fluid, the apparatus comprising:
   a pipe section, comprising an envelope through which a flow of the fluid is coupled between a tank of an electrical power device and a cooling device, the envelope disposed about a longitudinal axis, and one or more penetrations in the envelope, the one or more penetrations disposed laterally in relation to the longitudinal axis;
   a valve comprising an outlet, an inlet disposed opposite from the outlet along a longitudinal axis of the valve and attached to the pipe section, coupled with one of the one or more penetrations, and a solid spherical disk penetrated with a hollow tubular conduit aligned with a diameter of the disk, wherein an open state of the valve corresponds to a position of the disk in which the conduit aligns with the outlet and the inlet; and
   one or more instruments, each of the instruments comprising a housing component, a probe attached to the housing component and protruding therefrom, and a fitting and seal assembly attached to the housing component, each of the instruments operable for sensing one or more properties of a fluid flowing between the power device and a cooling device through the pipe section, wherein:
   a.) the probe comprises one or more sensors, each of the sensors operable for detecting at least one of the properties of the fluid and generating a detection signal corresponding to each of the detected fluid properties, and a conductor over which the generated detection signals are transmitted into the attached housing assembly,
   b.) the housing assembly comprises one or more detection signal processors, each of the processors operable for processing at least one of the detection signals transmitted into the housing assembly by the conductor and for generating a corresponding processed data signal, and a transmission component operable for generating an instrument output signal corresponding to each of the processed data signals, and
   c.) the attachment fitting and seal assembly fastens the housing assembly directly and removably to the outlet of the valve, the inlet disposed axially opposite from the outlet and attached to the pipe section, and the solid spherical disk penetrated diametrically with the hollow tubular conduit wherein, with the valve in the open state, and upon insertion of the probe through the valve and attachment of the attachment fitting and seal assembly to the outlet of the valve, the probe is immersed within the flow of the fluid through the pipe section.

2. The apparatus as described in claim 1, wherein the pipe section is disposed between opposing sections of a header through which the fluid flow is coupled between the power device tank and the cooling device.

3. The apparatus as described in claim 2, wherein the header comprises at least one of a lower header or an upper header, relative to one or more of each other, a corresponding lower vertical position on one or more of the power device tank or the cooling device, or a corresponding upper vertical position on one or more of the power device tank or the cooling device.

4. The apparatus as described in claim 2, wherein the pipe section is fastened between the opposing sections of the header.

5. The apparatus as described in claim 1, wherein the valve comprises a ball valve.

6. The apparatus as described in claim 1, wherein the probe of the one or more instruments is disposed, removably, through the valve.

7. The apparatus as described in claim 1, wherein the probe of the one or more instruments is interchangeable, through the valve, with a probe of at least a second instrument.

8. The apparatus as described in claim 1, wherein the one or more fluid properties comprises one or more of a physical characteristic, or a chemical characteristic of the fluid, and wherein the probe of the one or more instruments is operable for detecting at least two of the physical or chemical characteristics of the fluid.

9. The apparatus as described in claim 1 wherein the pipe section further comprises a first flange attached to a first end of the envelope and a second flange attached to a second end of the envelope opposite from the first end.

* * * * *